United States Patent [19]

Szekely et al.

[11] Patent Number: 4,638,002

[45] Date of Patent: Jan. 20, 1987

[54] 2,3,4-TRINOR-1,5-INTER-META-PHENYLENE-PROSTACYCLIN COMPOUNDS USEFUL IN INHIBITING THROMBOCYTE AGGREGATION

[75] Inventors: Istvan Szekely, Dunakeszi; Sandor Botar, Budapest; Krisztina Dolgos nee Kekesi, Debrecen; Bela Bertok, Dombovar; Antal Gajary, Budapest; Tamas Szabolcsi, Budapest; Gabor Kovacs, Budapest; Marianna Lovasz nee Gaspar, Budapest, all of Hungary

[73] Assignee: Chinoin Gyogyszer es Vegyeszeti Termekek Gyara Rt., Budapest, Hungary

[21] Appl. No.: 576,399

[22] PCT Filed: May 6, 1983

[86] PCT No.: PCT/HU83/00021

§ 371 Date: Dec. 30, 1983

§ 102(e) Date: Dec. 30, 1983

[87] PCT Pub. No.: WO83/04021

PCT Pub. Date: Nov. 24, 1983

[30] Foreign Application Priority Data

May 6, 1982 [HU] Hungary .............................. 1421/82

[51] Int. Cl.[4] .................. A61K 31/44; C07D 307/935
[52] U.S. Cl. ................................... 514/212; 514/382; 514/460; 514/469; 548/253; 548/252; 549/414; 549/415; 549/465; 560/56; 562/466; 564/172; 540/596; 540/607; 558/416; 558/123; 558/419
[58] Field of Search ...................... 549/465, 415, 414; 424/283, 285, 269; 514/469, 382, 212, 460; 548/253; 260/239.3 R

[56] References Cited

U.S. PATENT DOCUMENTS 4,372,971 2/1983 Seipp et al. .................... 514/469
4,451,483 5/1984 Szekely et al. ................. 514/469
4,479,945 10/1984 Szekely et al. ................. 549/465

*Primary Examiner*—Henry R. Jiles
*Assistant Examiner*—Bernard I. Dentz
*Attorney, Agent, or Firm*—Karl F. Ross; Herbert Dubno

[57] ABSTRACT

The invention relates to new 2,3,4-trinor-1,5-inter-m-phenylene-PGI$_2$ derivatives of the formula (I)

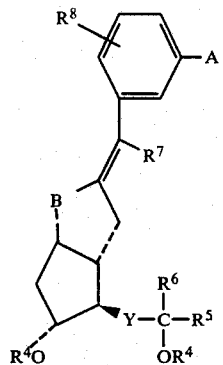

wherein

A stands for carboxy, cyano, tetrazolyl or —COOR$^3$ or —CONR$^1$R$^2$;

R$^3$ is C$_{1-4}$ alkyl or an equivalent of a pharmacologically acceptable cation:

R$^1$ and R$^2$ each stands for hydrogen, phenyl; C$_{1-5}$ alkyl, optionally substituted by carboxy, hydroxy, phenyl or C$_{2-5}$ alkoxycarbonyl; or C$_{1-4}$ alkylsulfonyl; or R$^1$ and R$^2$ together form an α,ω-alkylene chain containing 3–6 carbon atoms;

B stands for oxygen or methylene;

Y is optionally bromo-substituted vinylene or a —C≡C— group:

R$^4$ stands for hydrogen or tetrahydro-pyran-2-yl;

R$^5$ represents an alkyl group containing 5–9 carbon atoms, which can be optionally interrupted by one or more oxygen atom(s) or —CH=CH— or —C≡C— group(s) and/or optionally substituted by halogen; or a phenyoxymethyl group optionally substituted by halogen or trifluoromethyl; or an alkenoyloxymethyl group containing 3–5 carbon atoms;

R$^6$ is hydrogen or C$_{1-4}$ alkyl;

R$^7$ stands for hydrogen, halogen, cyano, C$_{1-4}$ alkyl or C$_{1-4}$ alkoxy;

R$^8$ is hydrogen, halogen, cyano, nitro, hydroxy or C$_{2-5}$ alkanoylamido;

with the proviso that if

R$^5$ stands for an alkyl group containing 5–9 carbon atoms which is unsubstituted or not interrupted by an oxygen atom or a —CH=CH— or —C≡C— group; or a phenyoxymethyl group optionally substituted by halogen or trifluoromethyl, then either R$^7$ or R$^8$ is other than hydrogen, or A is other than carboxy or —COOR$^3$ and a process for the preparation thereof.

The new compounds of the Formula I exhibit prolonged cytoprotecting and aggregation inhibiting and a low hypotensive effect and are superior to prostacycline in the prolonged duration of their activity.

6 Claims, No Drawings

2,3,4-TRINOR-1,5-INTER-META-PHENYLENE-PROSTACYCLIN COMPOUNDS USEFUL IN INHIBITING THROMBOCYTE AGGREGATION

This invention relates to new 2,3,4-trinor-1,5-inter-m-phenylene-prostacyclin-$I_2$ analogues, a process for the preparation thereof and pharmaceutical compositions containing the same.

According to an aspect of the present invention there are provided new 2,3,4-trinor-1,5-inter-m-phenylene-$PGI_2$ analogues of the Formula I

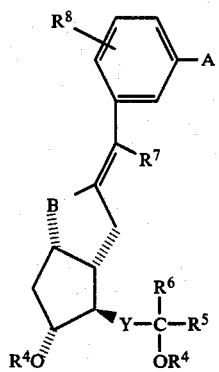

wherein
A stands for carboxy, cyano, tetrazolyl or —$COOR^3$ or —$CONR^1R^2$;
$R^3$ is $C_{1-4}$ alkyl or an equivalent of a pharmacologically acceptable cation;
$R^1$ and $R^2$ each stands for hydrogen, phenyl; $C_{1-5}$ alkyl, optionally substituted by carboxy, hydroxy, phenyl or $C_{2-5}$ alkoxycarbonyl; or $C_{1-4}$ alkylsulfonyl; or
$R^1$ and $R^2$ together form an $\alpha, \omega$-alkylene chain containing 3–6 carbon atoms;
B stands for oxygen or methylene;
Y is optionally bromo-substituted vinylene or a —C≡C— group;
$R^4$ stands for hydrogen or tetrahydro-pyran-2-yl;
$R^5$ represents an alkyl group containing 5–9 carbon atoms, which can be optionally interrupted by one or more oxygen atom or —CH=CH— or —C≡C— group and/or optionally substituted by halogen; or a phenyoxymethyl group optionally substituted by halogen or trifluoromethyl; or an alkenyloxymethyl group containing 3–5 carbon atoms;
$R^6$ is hydrogen or $C_{1-4}$ alkyl;
$R^7$ stands for hydrogen, halogen, cyano, $C_{1-4}$ alkyl or $C_{1-4}$ alkoxy;
$R^8$ is hydrogen, halogen, cyano, nitro, hydroxy or $C_{2-5}$ alkanoylamido;
with the proviso that if
$R^5$ stands for an alkyl group containing 5–9 carbon atoms which is unsubstituted or not interrupted by an oxygen atom or a —CH=CH— or —C≡C— group; or a phenyoxymethyl group optionally substituted by halogen or trifluoromethyl, then either $R^7$ or $R^8$ is other than hydrogen, or A is other than carboxy or —$COOR^3$ and salts thereof formed with pharmaceutically acceptable cations.

The prostacyclin analogues of the Formula I possess various valuable pharmacological properties. It is known that prostacyclin is a substance which occurs in nature and is biologically highly active. Prostacyclin plays a role in the regulation of haemostasis (antiaggregation, desaggregation), exhibits useful peripherial vasodilating effect as well as a generally acknowledged cytoprotective activity (Prostaglandins 1976, 12, 915–928; J. Am. Chem. Soc. 1977, 99, 2006; Pharmacol. Rev. 1968, 20, 1.).

The greatest drawback of the therapeutical use of prostacyclin resides in its great instability due to the enolether structural unit. Thus the half-period of the sodium salt of prostacyclin in aqueous solution at a pH value of 7 amounts to 3 minutes (Prostaglandins 1978, 15, 943).

Research in the field of prostacyclin analogues has been directed from the very beginning to the preparation of stable compounds having high prostacyclin activity.

According to DOS No. 3.029.984 the unstable prostacyclin structure can be stabilized by substituting the carbon chain between carbon atoms 1 and 5 (according to the numbering used in prostaglandin chemistry) by an aromatic ring. The derivatives thus obtained exhibit anti-aggregation and hypotensive effects and influence the heart rate; the said derivatives are more stable than $PGI_2$ occurring in nature. Compounds having substantially similar structure are disclosed in DOS No. 2.945.781. The said prostacyclin derivatives contain 1,2-phenylene group and according to the disclosure of DOS No. 2.945.781 they exert smooth muscle stimulating, blood platelet aggregation inhibiting and hypotensive effects, they inhibit the secretion of gastric acid, exhibit an antiasthma effect, heal the lesions caused by non-steroidal anti-inflammatory agents and show an antidermatosis effect as well. The strength and duration of the activities is, however, not disclosed in the cited references.

According to European Patent Application No. 0,062,902 the ratio of the hypotensive and blood platelet aggregation inhibiting effects can be shifted in favor of the latter activity by introducting into the lower side-chain an alkyl group being longer than that of natural $PGI_2$ or an amino or optionally a phenyl or benzyl group.

The strength of the above two basic biological activities can be altered to a still larger extent by replacing the vinylene group in position 13, 14 (according to the numbering used in prostaglandin chemistry) by a halogenated vinylene group or an acetylene group and simultaneously using a side-chain being longer or comprising an aromatic group, respectively (European Patent Application No. 82,110,986). The antiaggregation effect of the said compounds is approximately similar to that of $PGI_2$ while—on the other hand—the undesired hypotensive effect is about 200–230 times weaker than that of $PGI_2$.

It has been surprisingly found that the new 2,3,4-trinor-1,5-inter-m-phenylene-$PGI_2$ derivatives of the Formula I of the present invention are significantly superior to the known $PGI_2$ analogues of similar structure. Thus the compounds of the present invention show a significantly higher cytoprotective activity, the duration of the effect is longer and when tested on the Szekeres antiangina model (J. Pharm. Exp. Ther. 15, 196- (1976)) they show a significant protecting effect for 5 hours after i.v. administration.

The cytoprotective effect is tested according to the method of A. Robert et al (Gastroenterology 77, 433-

(1979)). As test compounds derivatives of the Formula I are used in which A is —COONa, $R^8$ is hydrogen, B stands for oxygen, $R^4$ is hydrogen, Y represents —C≡C—, $R^6$ is hydrogen and $R^5$ stands for n-hexyl. In the following Table I the doses (in mg/kg body weight) of the compounds are disclosed which show significant cytoprotecting effect. The said compounds differ from each other in the definition of symbol $R^7$. The first compound—in which $R^7$ is hydrogen—is disclosed in European Patent Application No. 82,110,986.

TABLE I

| $R^7$ | Dose of significant cytoprotective effect in ug/kg body weight |
|---|---|
| H— | 600 |
| F— | 25 |
| Cl— | 25 |
| CH$_3$—O— | 125 |
| —CN | 5 |

It appears from the above Table that the compounds of the present invention exhibit a significantly stronger cytoprotecting activity.

It is known that when administering PGI$_2$ to cats in an intravenous dose of 10 μg/kg a hypotensive effect (6.6 kPa=50 Hgmm) is observed, the duration of the effect is, however, very short, the activity ceases after about one minute and a half. In order to determine the duration of the effect the said activity, which can be easily followed instrumentally, is measured. Since the hypotensive effect of the compounds of the present invention is lower than that of PGI$_2$, the active ingredient is administered in an intravenous dose of 100 μg/kg and the time is measured during which the blood pressure of the cats returns to the original value. The above data (in minutes) are set forth in Table II. In all the test compounds A is —COONa, $R^7$ stands for hydrogen, B is oxygen, $R^4$ represents hydrogen, Y is —C≡C— and $R^6$ stands for hydrogen. The variable groups $R^8$ and $R^5$ are disclosed in Table II. The first compound ($R^8$ is hydrogen and $R^5$ stands for n-hexyl) is described in European Patent Application No. 82,110,986.

TABLE II

| $R^8$ | $R^5$ | Time required for the blood pressure to return to the original value, in minutes |
|---|---|---|
| H— | n-hexyl- | 4 |
| F— | n-heptyl- | 10 |
| Cl— | n-octyl- | 6 |
| —CN | n-heptyl- | 12 |
| —NO$_2$ | n-octyl- | 16 |
| H— | 2-methyl-4-pentyn-1-yl- | 10 |
| H— | 6-methyl-5-hepten-1-yl- | 16 |
| H— | —CH$_2$—O—CH$_2$—CH$_2$—O—CH$_3$ | 19 |
| H— | —CH$_2$—O—CH$_2$—CF$_3$ | 16 |

A similar prolongation of the duration of the effect is detected on at ex-vivo anti-aggregation model as well (Arch. int. Pharmacodyn. 259, 310–311 (1982)).

The anti-aggregation effects of the compounds of the present invention almost reach those of prostacyclin. For the sake of illustration the IC$_{50}$ values (measured on human PRP, in ng) and IC$_{100}$ values (measured on guinea pig PRP, in ng/ml) of some compounds are disclosed below:

(a) 2,3,4-trinor-1,5-inter-m-phenylene-13,14-didehydro-20-methyl-Δ$^{19}$-PGI$_2$, 4.9 and 6 respectively;

(b) 2,3,4-trinor-1,5-inter-m-phenylene-13,14-17,18-bis-didehydro-20-methyl-PGI$_2$ sodium salt, 6 and 8.2 respectively;

(c) 2,3,4-trinor-1,5-inter-(4-fluoro-1,3-phenylene)-13,14-didehydro-20-methyl-PGI$_2$-sodium salt, 6.2 and 10 respectively.

Moreover the above compounds show a greater stability. Thus on compound (c) practically no decomposition can be detected which is particularly advantageous since it enables the administration of the active ingredients in physiological sodium chloride solution too, contrary to prostacyclin, which cause vasculitis in an alkaline medium. The haemodinamic side-effect of the compounds of the present invention is lower than that of prostacyclin by an order of magnitude.

The biological activity of the new prostacyclin analogues of the present invention is comparable to that of prostacyclin, while the chemical stability thereof is significantly better and the compounds are stabilized against the so-called "β-oxidation" and "15-PGDH" metabolismus being responsible for the rapid decomposition of the active ingredient.

The compounds of the Formula I show strong biological activity and possess valuable and useful pharmacological properties. Thus the said compounds exert i.e. the following effects: they inhibit the aggregation of blood platelets and the secretion of gastric acid, decrease the undesired gastrointestinal effects of pharmaceutical compositions comprising prostaglandin synthetaze inhibitor, in asthmatic states they relieve bronchial spasms and make respiration easier.

Due to the above useful biological activities the compounds of the Formula I can be used in the study, treatment and prevention of various diseases and undesired physiological states. Thus the compounds of the Formula I are useful e.g. in the inhibition of blood platelet aggregation, modification of the adhesion properties of blood platelets, removal of clots, and inhibition of the formation of clots. The compounds of the Formula I can be used in the treatment and prevention of cardiac infarction, treatment of thrombus formation problems in connection with arteriosclerosis, hyperlipemia or lipemia, or in lengthly prophylactic treatments after cardiac infarction or cerebral haemorrhage.

The compounds of the Formula I when added to "complete blood" in artificial heart or kidney inhibit the clot formation, and thus enable the perfusion of the organic used in transplantation with blood without the risk of clot formation. Moreover the compounds of the Formula I can be used for the preparation of blood concentrates enriched in blood platelets suitable for thrombocytapemial and chemotherapeutic purposes.

The compounds of the Formula I are highly suitable for the treatment of diseases of peripherial vascular system. The term "peripherial vascular system" used in the present patent specification comprises all blood vessels except the heart. Thus the compounds of the Formula I are useful in the healing and treatment of freezing, frostbites, insufficiency of cerebral blood supply, ulcers caused by insufficient blood supply to the extremities, phlebitis, venous insufficiency, necrosis etc.

The compounds of the Formula I can be used as hypotensive agents too.

The compounds of the present invention decrease and regulate the excessive secretion of gastric acid and thereby decrease or inhibit ulcer formation in the gastrointestinal tract. Thus the healing of ulcers can be accelerated to a large extent.

In addition to the above activities the compounds of the Formula I can decrease the undesired ulcerative effects of prostaglandin synthetaze inhibitors to a significant extent. Thus on administering indomethacin, aspirin, phenylbutazone etc. simultaneously with a compound of the Formula I, the desired anti-inflammatory effect of the said drugs remain maintained while their ulcerative and other undesired side-effects decrease to a significant extent or even disappear completely.

The compounds of the Formula I are useful in the treatment of asthma. In addition to the bronchodilatory and bronchial spasmolytic activities, the compounds of the present invention inhibit the histamine effect of mediators (e.g. SRS-A).

According to a further feature of the present invention there are provided pharmaceutical compositions comprising an effective amount of a compound of a Formula I or a therapeutically acceptable salt thereof in admixture with suitable inert pharmaceutical carriers and optionally with further therapeutically active compounds.

The pharmaceutical compositions of the present invention for use against asthma can be finished in the usual systematic administration forms (suitable for intravenous, subcutaneous, oral, intramuscular or parenteral administration) and also as aerosol comprising a compound of the Formula I per se or in combination with further therapeutically active compounds.

The pharmaceutical compositions according to the present invention can be solid, semi-solid or liquid. The pharmaceutical compositions can be finished in forms known per se by known methods of the pharmaceutical industry, i.e. e.g. as lotions, drops, liquid medicines to be taken with a spoon, aerosols, tablets, pills, coated pills, dragées, powders, granules, ointments, suppositories, etc.

The pharmaceutical composition can be prepared by admixing at least one compound of the Formula I with diluents, carriers, additives and auxiliary agents (e.g. agents for stabilizing the pH value, color, osmotic pressure, agents for improving the taste, flavorants etc.) generally used in the pharmaceutical industry. The mixture thus obtained may be converted into a ready-for-use pharmaceutical composition by methods known per se.

The compounds of the Formula I are preferably finished in the form of dosage units which contain an amount of the active ingredient capable of exhibiting the desired therapeutical effect. The dosage units can also comprise a part or a multiple amount of the dosage required and may be finished in forms which facilitate the division of the dosage (e.g. divided tablets).

The active ingredient content of the dosage units can vary between wide ranges. The active ingredient dose used depends on the field of application. Thus a single dose is generally between 0.01 µg/kg body weight and 100 µg/kg body weight. The actual dose depends on the individual sensitivity of the human or animal to be treated, the gravity of the disease, the mode of administration etc. The actual determination of the actual dose falls under the routine knowledge and practice of the physician.

According to a further feature of the present invention there is provided a process for the preparation of the 2,3,4-trinor-1,5-inter-m-phenylene-PGI$_{2\alpha}$ derivatives of the Formula I which comprises (a) for the preparation of compounds of the Formula I, in which B stands for oxygen, reacting a lactol of the Formula II

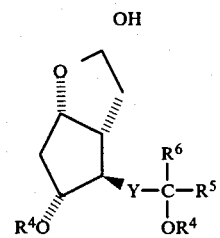

with a phosphorane formed from a phosphonium salt of the Formula III

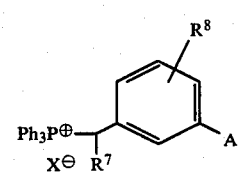

Ph is phenyl and X$^-$ is monovalent anion) with a strong base;

reacting the 2,3,4-trinor-1,5-inter-m-phenylene-PGF$_{2\alpha}$ derivative of the Formula IV thus obtained

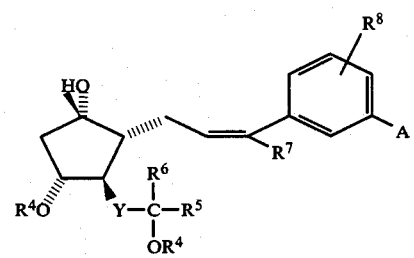

with an electrophilic reagent of the FOrmula E-X wherein E is halogen or a phenyl-selenyl group and X is halogen or a 2,5-dioxo-pyrrolidin-1-yl group; thereafter subjecting the 2,3,4-trinor-1,5-inter-m-phenylene-PGI$_1$ derivative of the Formula V thus obtained

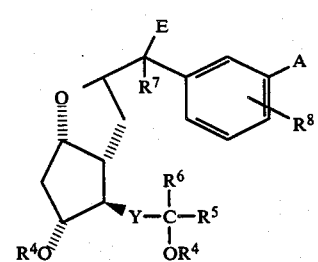

to an elimination reaction; or (b) for the preparation of compounds of the Formula I, wherein B is methylene, reacting a ketone of the formula VI

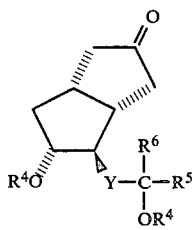

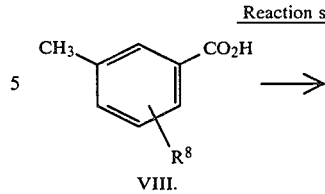

Reaction scheme 1

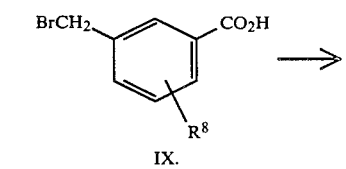

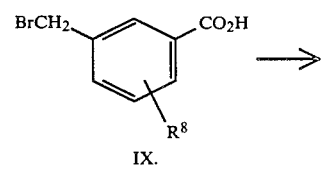

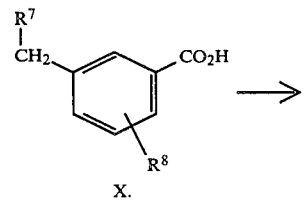

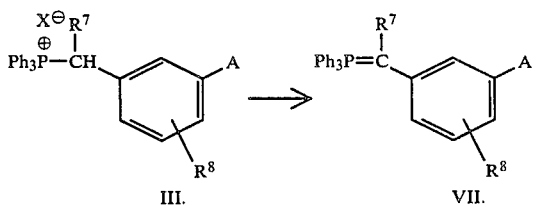

with a phosphorane formed from a phosphonium salt of the Formula III with a strong base, and if desired converting a 2,3,4-trinor-1,5-inter-m-phenylene-PGI$_2$ derivative of the Formula I thus obtained into an other compound of the Formula I by saponification, salt formation, amidation, dehydration, hydrolysis or tetrazolyation and/or if desired separating the isomers from a mixture thereof.

The prostaglandin and carbaprostacyclin intermediates of the Formulae II and VI, respectively, used as starting material are known compounds.

In the case of a bicyclo[3.3.0] octanone of the Formula VI, on subjecting a phosphorane of the Formula VII

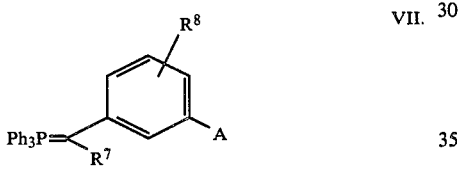

obtained by treating a phosphonium salt of the Formula III with a strong base according to the Wittig reaction, the compounds of the Formula I, in which B is methylene, are directly obtained.

On using a compound of the Formula II as starting material, the Wittig reaction of the phosphorane of the Formula VII yields a PGF$_{2\alpha}$-derivative of the Formula IV which is reacted with an electrophilic agent of the Formula E-X to give a PGI$_1$ analogue of the Formula V. The compound thus obtained is converted into an end-product of the Formula I comprising an enolether group by treatment with a tertiary amine or sodium or potassium superoxide, sodium or potassium carbonate, sodium or potassium hydroxide, sodium or potassium benzoate, sodium or potassium acetate, sodium or potassium trifluoroacetate, sodium or potassium hydrogen carbonate, silver acetate or a tetraalkyl ammonium superoxide reagent.

The carboxy group in position 1 of the compounds of the Formula I thus obtained can be esterified into an ester group, reduced into an alcohol, converted into an amide or sulfonamide in the frame of the substituent definition of the general Formula I by methods known per se or by methods described in the present patent specification.

The details of the preparation of the compounds of the present invention are disclosed below:

Reaction scheme 2

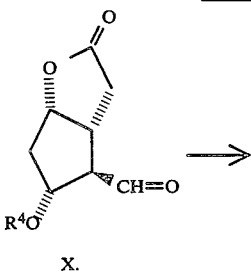

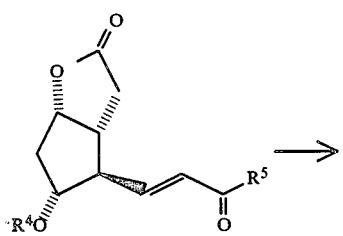

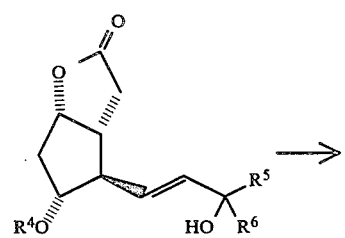

-continued
Reaction scheme 2

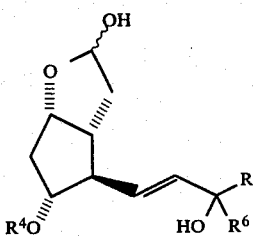

Reaction scheme 3

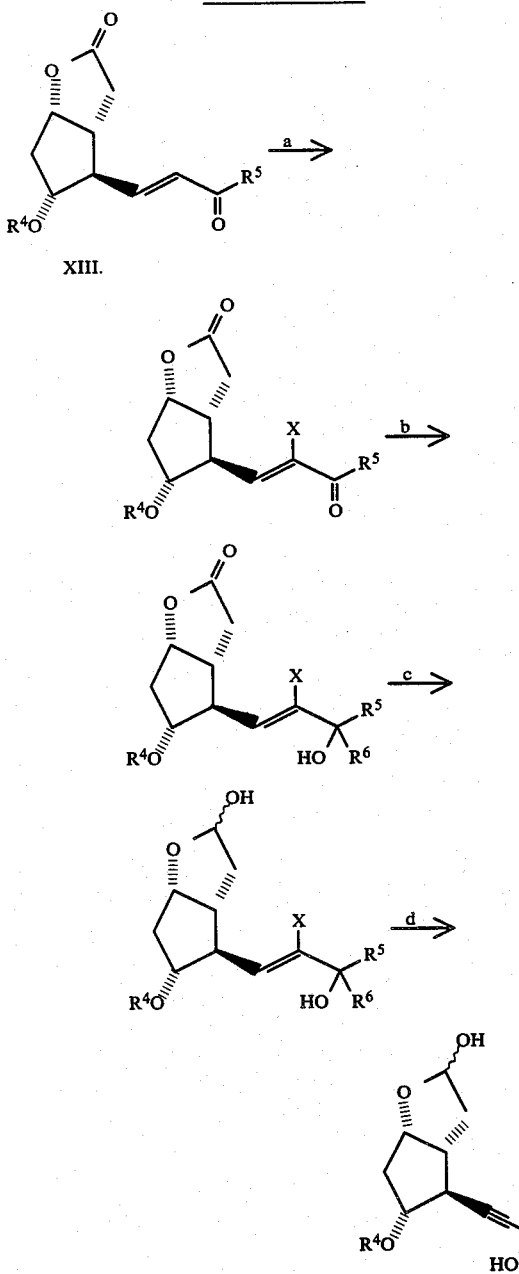

The preparation of the Wittig reagents used in the synthesis is shown in Reaction Scheme 1. As starting material m-methyl-benzoic acid and derivatives thereof of the Formula VIII are used. The various compounds corresponding to the definition of symbol $R^8$ are known from the prior art. [Beilstein 9, 478–480., Berichte 62, 1813 (1929), JACS. 1940, 62, 2188-., JACS 1933, 55, 716-, Berichte 1907, 40, 4409-, Berichte 1881, 14, 2347-, Berichte 1885, 18, 360-, Berichte 1906, 39, 73-, Berichte 1909, 42, 430-, Berichte 1905, 38, 3554].

In the first step a compound of the Formula VIII is halogenated—preferably brominated. The halogenation is carried out by methods of benzyl halogenation known per se (Organikum page 151, edited by Müszaki Könyvkiadó, Budapest 1967). The m-bromomethyl benzoic acid derivatives of the Formula IX can be preferably prepared by heating to boiling a compound of the Formula VIII with N-bromo succinimide in carbon tetrachloride.

The $R^7$ substituent is introduced in the second step by means of a nucleophilic substitution reaction. Thus the alkyl, alkoxy and nitrile groups can be introduced by reacting a compound of the Formula IX with a suitable nucleophilic reactant, e.g. with the corresponding alkyl cuprate or alkoxy or cyanide salt, respectively. The said reaction is carried out by methods known per se. Due to the known high reactivity of the benzyl halides the said reaction can be carried out with excellent yields.

Similarly the bromine-fluorine exchange reaction can be carried with quantitative yields too. The said reaction can be accomplished e.g. with a potassium fluoride reagent, in acetonitrile in the presence or absence of a 18 crown-6 catalyst (J. Am. Chem. Soc. 1974, 96, 2250–2253).

The third reaction step is also a halogenation reaction, wherein a "benzyl halide" is prepared corresponding to the first reaction. The reaction can be preferably accomplished by using N-bromo succinimide and the corresponding substituted m-carboxy-benzyl-bromides are obtained.

The carboxy group of the compounds thus obtained can be converted into a carboxamido, substituted carboxamido, sufonated carboxamido, tetrazolyl or esterified carboxy group by methods known per se. In the course of the process of the present invention the said groups remain uneffected and unchanged.

It is evident that the latter substituents can also be introduced at a later stage of the synthesis.

The phosphonium salts are prepared by method known per se, e.g. by heating to boiling a mixture of a benzyl halide derivative thus obtained and triphenyl phosphine in benzene, toluene, xylene or an other aprotic organic solvent.

The phosphonium salts are generally isolated in the form of white crystals by filtering the reaction mixture.

The phosphoranes of the Formula VII to be used in the Wittig reaction are prepared in situ with the aid of a strong base. For this purpose preferably sodium methyl sulfenyl methide, potassium methyl sulfenyl methide, or sodium amide can be used, in the presence of a polar aprotic solvent, such as dimethyl formamide, dimethyl sulfoxide etc.

The phosphonium salts of the Formula III can also be prepared from the phosphoranes of the Formula VII by using an electrophilic $R^7$ reagent. Thus one may proceed by adding perchloryl fluoride or introducing chlorine gas etc. to a solution of the phosphorane and dimethyl sulfoxide to yield the compounds of the Formula III comprising the corresponding fluoro or chloro substituent.

The bromo or chloro substituents ($R^7$) of the phosphonium salts of the Formula III can be replaced in substitution reactions. Thus the intermediates of the Formula III, in which $R^7$ is bromine or chlorine, can be converted into the corresponding phosphonium salts of the Formula III in which $R^7$ represents fluorine, cyano or alkoxy.

The procedures relating to the various definitions of Y are disclosed in "The Synthesis of Prostaglandins, Ed. A. Mitra: John Wiley and Sons, 1977, pages 379-381" and "Bindra and Bindra Prostaglandin Synthesis, 1977, Academix Press Inc. III. Fifth Avenue, New York N.Y. 10003, pages 199-210".

According to the process illustrated on Reaction Scheme 2 a bicyclic lactone aldehyde of the Formula X is reacted with a phosphorane of the Formula XI; from the bicyclic enone of the Formula XIII in the next reaction step the bicyclic lactone comprising an allyl alcohol structural unit is formed by using a nucleophilic reagent; and the product thus obtained is reduced into the corresponding bicyclic lactol of the Formula II, wherein Y is a group of the Formula —CH=CH—, in the next reaction step, preferably with diisobutyl aluminium hydride.

Starting materials of the Formula II comprising a halogen atom in position 14 can be prepared by halogenation in the presence of pyridine or another suitable base as shown in the first step of Reaction Scheme 3 (and by further transformations already shown on reaction scheme 2).

The —C≡C— group can be formed from compounds of the Formula II or I comprising a bromine atom in position 14 by treatment with a suitable base, e.g. potassium tertiary butoxide.

The preparation of compounds of the Formula II bearing various optional substituents in position 15 is disclosed in the prior art in a number of encyclopedical works (see. e.g. Bindra and Bindra: Prostaglandin Synthesis, 1977, Academic Press Inc. III. Fifth Avenue, New York, 10003, 203-210, and also in J. Am. Chem. Soc. 1974, 96, 5685-, Prostaglandins, 1974, 6, 207-,).

The desired allyl alcohol sturctural element can be formed by using generally known methods by subjecting a bicyclic enone of the Formula XIII to nuclophilic 1,2-addition reaction.

The preparation of compounds of the Formula II bearing the given $R^5$ substituents is described i.e. by Bindra and Bindra: Prostaglandin Synthesis, 1977, Academic Press In. III. Fifth Avenue, New York, 10003, 470 and 472-473. Some methods of preparation are disclosed in the present patent specification too.

The bicyclo octane derivatives of the Formula VI can be prepared from the compounds of the Formula II by known methods (J. Org. Chem. 1981, 46, 1954-1957).

The Wittig reaction of the present invention of the bicyclic lactol derivatives of the Formula II can be carried out with excellent yields in a strong polar aprotic solvent, e.g. hexamethyl phosphoric acid triamide (J. Am. Chem. Soc. 1969, 91, 5675-, 1971, 93 1489; 1970, 92, 397-). The Wittig reaction can also be accomplished in excellent yields by using phosphoranes in which A stands for a carboxamido, substituted carboxamido, sulfonamido or tetrazolyl group.

In the next step the compound of the Formula IV thus obtained is reacted with an electrophilic agent and subjected to cyclization. Thus $PGI_1$ analogues of the Formula V are obtained. The derivatives, in which E stands for halogen atom, can be prepared by several methods.

The derivatives in which E stands for a iodine atom can be prepared preferably by using a two-phase system comprising an aqueous and organic phase. The iodine can be added in the form of a solution formed with dichloro ethane and the aqueous layer may comprise potassium iodine and alkali metal carbonate or alkali metal hydrogen carbonate. If the $PGF_2$ analogue of the Formula IV is added to the above system, the reaction takes completely place within 1-20 hours at 0°-25° C. under stirring. The excess of iodine is reduced with sodium sulfite or sodium thiosulfate to iodine and the compound of the Formula V thus obtained is isolated by extraction.

The compounds in which E is a bromine atom can be prepared by using N-bromo-succinimide or N-bromoacetamide. The reaction can be preferably accomplished in a solvent mixture consisting of tetrahydrofuran and chloroform (Fieser and Fieser Reagents for Organic Synthesis, Vol. 1. pages 74-78, Vol. 4., page 51.: John Wiley and Sons, Inc. N.Y.).

The compounds in which E is a chlorine atom can be prepared by replacing the bromine atom of compounds of the Formula V, in which E is bromine, by chloride with e.g. a chloro-difluoro-acetic acid silver salt (Compendium of Org. Synth. Methods page 346, 1971, Wiley interscience N.Y.).

The compounds of the Formula V may be also obtained by cyclization reactions induced by other electrophilic reactants. On using a phenyl selenyl halide reactant in the cyclization reaction the corresponding phenyl selenyl derivatives of the Formula V are obtained, in which E stands for PhSe. The above reactions are carried out preferably in an aprotic organic solvent (e.g. tetrahydrofurane, chloroform, methylene chloride etc.).

In the above reaction the compounds of the Formula V are obtained in the form of a mixture of two epimers which show different chromatographic mobility. In the process of the present invention the separation of the said C-6 epimers is not necessary because both epimers can be converted into the desired products of the Formula I.

Compounds of the Formula V, in which E is halogen, can be converted into the desired end-products of the Formula I by means of dehydrohalogenation.

The hydrogen halide can be split off by using generally known dehydrohalogenating agents (see e.g. Fieser and Fieser: "Reagents for Organic Syntheses 1" page 1308, 1967, John Wiley and Sons Inc. N.Y.).

The said elimination reaction can be carried out by using tertiary amines or sodium or potassium hydroxide, sodium or potassium carbonate, sodium or potassium hydrogen carbonate, sodium or potassium superoxide, sodium or potassium acetate, sodium or potassium benzoate, sodium or potassium trifluoroacetate, sodium, potassium or lithium alcoholate, silver acetate, tetraalkyl ammonium superoxide etc.

As tertiary amine preferably 1,5-diazabicyclo[4.3.0]-nonen-5, 1,4-diazabicyclo[2.2.2]octane (DABCO) or 1,5-diazabicyclo[5.4.0]undec-5-en (DBU) can be applied.

Further reagents suitable for use in the above elimination reaction are the sodium butoxide, potassium tertiary butoxide, sodium isoamyloxide in dimethyl sulfoxide, tetrahydrofuran or benzene as solvent, or sodium or potassium methyl sulfenyl methide (DIMSYL-Na or DIMSYL-K) in dimethyl sulfoxide, and also the sodium or potassium tetramethyl ammonium superoxide (J. Org. Chem. 1975, 40, 1680).

The elimination of hydrogen halide can be carried out in an inert gas atmosphere at a temperature between 0° C. and 50° C., preferably at room temperature. The reaction can be followed and checked by means of layerchromatography.

The reaction mixture obtained in the elimination reaction can be worked up by different methods.

If the product contains a free carboxy group, the product can be crystallized in the presence of sodium ions in the form of the sodium salt and the impurities can be removed with the mother-lye.

Compounds of the Formula I containing a free carboxy group (A stands for carboxy) are converted into a carboxylate in the course of the dehydrohalogenation reaction. The free carboxylic acid can be isolated by acidifying carefully the solution of the compound comprising a carboxylate group and subjecting the aqueous solution to extraction.

If carboxamides or sulfonamides of the Formula V are subjected to the dehydrohalogenation reaction, the group A remains uneffected.

Compounds of the Formula V in which A stands for an ester group of the Formula —COOR$^3$ may be subjected to the hydrogen halide elimination reaction in the presence of 1,5-diazabicyclo[4.3.0]nonen-5, 1,4-diazabicyclo[2.2.2]octane or 1,5-diazabicyclo[5.4.0]undec-5-ene, particularly if esters of the Formula I are to be prepared.

The esters, amides and sulfonamides thus obtaine of can be purified by column chromatography on silikagel G or Florisil columns.

If PGI$_1$ analogues of the Formula V wherein E stands for a phenyl selenyl substituent are used, the compounds of the Formula I are obtained by oxidizing the phenyl selenyl group into selenium dioxide and eliminating the latter by thermal methods.

In the above reactions it is preferred to use ester, carboxamide or sulfonamide derivatives. In this case after the termination of the elimination reaction the reaction mixture is diluted with water, the compound of the Formula I is extracted, the organic phase is washed with a sodium hydrogen carbonate solution and the compound of the Formula I is isolated by evaporation or chromatography.

The "A" group of a compound of the Formula I can be converted into an other group in the scope of the substituent definition of the Formula I after the formation of the enol ether structure.

Thus an ester obtained in the dehydrohalogenation reaction can be converted into a caroxylic acid by hydrolysis and the carboxylic acid can be transformed into an other eseter of the general Formula I.

Thus e.g. the alkyl esters can be prepared by reacting the carboxylic acid with the corresponding diazoalkane. The use of diazomethane leads to the formation of a methyl ester. In a similar manner when diazoethane or diazobutane are used, the corresponding ethyl and butyl esters are obtained, respectively.

The above esterification can be carried out by adding to the solution of the carboxylic acid formed in a suitable solvent (e.g. diethyl ether) the solution of the diazoalkane formed in a suitable organic solvent (e.g. diethyl ether) at a temperature between 0° C. and 20° C. After the termination of the reaction the solvent is removed and the ester of the Formula I thus obtained can be purified—e.g. by chromatography—if necessary.

The general method for the preparation of diazoalkanes is disclosed e.g. in Org. Reactions John Wiley and Sons, Inc. New York N.Y. Vol. 8 pages 389-394 (1954).

According to an other method the esters are prepared by converting the free carboxylic acid into its silver salt and reacting the said compound with the corresponding alkyl iodide. For this purpose e.g. methyl iodide, ethyl iodide, butyl iodide etc. can be used.

The silver salts can be prepared by dissolving the free caroxylic acid in a cold diluted aqueous ammonium hydroxide solution, removing the excess of ammonium in vacuo adding a stochiometrical amount of silver nitrate to the residue.

Compounds of the Formula I, in which A stands for a group of the Formula —CONR$^1$R$^2$, can be prepared by reacting the free carboxylic acid of the Formula I with a chloro formiate preferably with chloro isobutyl formiate in the presence of a suitable base (e.g. triethyl amine) and reacting the mixed anhydride thus obtained with ammonium or the corresponding base of the Formula HNR$^1$R$^2$.

The amides derived from amino acids can also be prepared by the above method. In this case the mixed anhydrides can be reacted with suitable protected amino acids.

The N-sulfonamides of the general Formula I (in which A stands for —CO—NR$^1$—SO$_2$—Alkyl) can be prepared by reacting the above mixed anhydride with a sulfonamide sodium salt obtained by treating the corresponding HNR$^1$—SO$_2$—Alkyl sulfonamide with sodium alcoholate. It is preferred to add hexamethyl phosphoric acid triamide to the reaction mixture in order to make the mixture homogenous.

Compounds of the Formula I, in which A stands for a tetrazolyl or cyano group, can also be prepared by the process of the present invention.

Nitriles can be prepared e.g. by subjecting the corresponding acid amide to dehydration. This reaction can be carried out e.g. by using carbodiimides by methods known per se (J. Org. Che. 1961, 26, 3354-). One may proceed preferably by reacting the corresponding acid amide with N,N'-dicyclohexyl carbodiimide in pyridine at 10°-50° C.

The nitriles of the Formula I thus obtained can be converted into the corresponding compounds of the Formula I, wherein A stands for a tetrazolyl group, by methods known per se by reacting with a reagent comprising sodium azide and ammonium chloride, in dimethyl formamide as medium (Heterocyclic Compounds, Editor: R. C. Eldvfield, John. Wiley and Sons Inc. N.Y. Vol. 8, pages 11-12). It is evident that the said compounds can also be prepared by using as starting material phosphorane derivatives of the Formula VII in which A stands for a tetrazolyl group.

In the salts of the compounds of the Formula I, A is a —COOR$^3$ group and R$^3$ stands for a pharmacologically acceptable cation e.g. a metal or ammonium cation or a primary, secondary, tertiary or quaternary ammonium cation. Preferred cations are e.g. the alkali metal cations (e.g. lithium, sodium or potassium cations), alkaline earth metal cations (e.g. magnesium or calcium cations), or other metal cations (e.g. aluminium, zinc or iron cations).

The pharmacologically acceptable organic cations may be formed e.g. with the following primary, secondary, or teriary amines which can be protonated to cations: methyl amine, dimethyl amine, trimethyl amine, ethyl amine, dibutyl amine, diisopropyl amine, triisopropyl amine, N-methyl-hexyl-amine, decyl amine, dodecyl amine, allyl amine, crotyl amine, cyclopentyl amine, cyclohexyl amine, dicyclohexyl amine, benzyl amine, dibenzyl amine, α-phenyl ethyl amine, β-phenyl ethyl amine, ethylene diamine, diethylene diamine and similar other aliphatic, cycloaliphatic or araliphatic amines up to a total carbon atom number of 18. Pharmacologically acceptable salts can also be formed with heterocyclic amines, e.g. piperidine, morpholine, pyrrolidine, piperazine and lower alkyl substituted derivatives thereof, such as 1-methyl-piperidine, 4-ethyl-morpholine, 1-isopropyl-pyrrolidine, 1,4-dimethyl-piperazine, 2-methyl-piperidine etc.

Further amines suitable for salt formation are those which contain a hydrophilic group promoting water-solubility e.g. mono- di- and triethanol amine, ethyl-diethanol amine, N-butyl-ethanol amine, 2-amino-1-butanol, 2-amino-2-ethyl-1,3-propane diol, 2-amino-2-methyl-1-propanol, tris-(hydroxymethyl)-aminomethane, N-phenyl-ethanol amine, 1-(p-nitro-phenyl)-2-methyl-1,3-propane diol, N-(p-tertiary amyl-phenyl)-diethanol amine, N-methyl-glucamine, N-methyl-glucosamine, ephedrine, phenyletrine, epinetrine, procaine etc.

As further phamacologically acceptably quaternary ammonium cations e.g. the tetramethyl ammonium, tetraethyl ammonium, benzyl trimethyl ammonium, phenyl triethyl ammonium cations etc. can be mentioned.

Further details of the present invention are to be found in the Examples without limiting the scope of the Examples which serve merely as illustration.

The $^1$H-NMR spectra disclosed in the Examples are taken up on a Bruker WP 80 SY FT spectrophotometer.

The thin layer characteristic data "$R_f$" indicate the displacement of the sample spot related to the displacement of the solvent front on a silicagel plate (unless otherwise stated) in the given solvent mixture. For all measurements Merck "Kieselgel 60 $F_{254}$" thin layer chromatography plates are used.

The silicagel columns (0.063-0.02 mm) used in the Examples are eluted, the fractions are collected and those fractions are pooled which contain the desired products and are free from starting materials and contaminants (according to layer chromatography analysis).

The term "working up" relates to the suspending or dissolving of the substance in an organic solvent, treating with an anhydrous dehydrating agent (e.g. sodium sulfate or magnesium sulfate) and filtering the suspension.

EXAMPLE 1

Preparation of 3-bromomethyl-benzoic acid 10 g (73.4 millimoles) of m-methyl-benzoic acid are dissolved in 75 ml of anhydrous carbon tetrachloride, whereupon 0.2 g of 2,2'-azo-bis-(2-methyl-propiontirile) and 13.72 g (77.07 millimoles) of N-bromo-succinimide are added. The reaction mixture is refluxed for 20 minutes, the formed succinimide is removed by filtering the warm mixture. The organic filtrate is washed with 15 ml of water, dried over sodium sulfate, filtered and the filtrate is evaporated in vacuo. The crude product thus obtained is recrystallized from a fivefold amount of carbon tetrachloride. Thus 12.71 g of the title compound are obtained, yield 80.5%.

Analysis data: Thin layer chromatography $R_f$=0.38 (a 1:1 mixture of benzene and ethyl acetate).

The $R_f$ value of the methyl ester prepared by using diazomethane amounts to 0.38 (a 2:1 mixture of benzene-hexane).

$^1$H-NMR/CDCl$_3$, δ/:4,51/s, 2H, CH$_2$/ 7.25-7.6 (m, 2H, aromatic protons), 7.75-7.85 (m, 2H, aromatic protons).

In an analogous manner to the above process the following compounds are prepared:
3-bromomethyl-6-nitro-benzoic acid, $R_f$=0,07 (a 1:1 mixture of benzene and ethyl acetate),
$^1$H-NMR (CDCl$_3$, δ/:4.54/s, 2H, CH$_2$) 7.5-8.1 (m, 3H, aromatic protons).
3-bromomethyl-4-fluoro-benzoic acid, $R_f$=0.36 (a 1:1 mixture of benzene and ethyl acetate);
2-chloro-3-bromomethyl-benzoic acid, $R_f$=0.35 (a 1:1 mixture of benzene and ethyl acetate);
3-bromomethyl-6-cyano-benzoic acid, $R_f$=0.32 (a 1:1 mixture of benzene and ethyl acetate);
3-bromomethyl-5-hydroxy-benzoic acid, $R_f$=0.15 (a 1:1 mixture of benzene and ethyl acetate);
3-bromomethyl-5-hydroxy-benzoic acid, $R_f$=0.05 (a 1:1 mixture of benzene and ethyl acetate).

EXAMPLE 2

Preparation of 3-methoxymethyl-benzoic acid 12 g (55.75 millimoles) of 3-bromomethyl-benzoic acid are dissolved in 10 ml of anhydrous methanol and to the solution 22.30 ml of sodium methylate (concentration 5 millimoles/ml) are added dropwise at room temperature. The reaction mixture is stirred for 5-10 minutes, the methanol is removed in vacuo. The residue is dissolved in 10 ml of ethyl acetate, to the solution 2 ml of water are added and the pH of the mixture is adjusted to 2-3 with a 2N sodium hydrogen sulfate solution at 0° C. The layers are separated, the organic phase is dried, filtered and the solvent is distilled off in vacuo. Thus 8.55 g of the title compound are obtained, yield 92,3%.

Analysis data: TLC: $R_f$=0.13 (a 1:1 mixture of benzene and ethyl acetate), $R_f$=0.61 (a 20:10:1 mixture of benzene, dioxane and acetic acid).

EXAMPLE 3

Preparation of 3-fluoromethyl-benzoic acid 2.945 g (11.15 millimoles) of 1,4,7,10,13,16-hexanona-cyclooctadecane (18-Crown-6) are dissolved in 30 ml anhydrous acetonitrile, whereupon 6.48 g (111.54 millimoles) of anhydrous potassium fluoride are added. The mixture is stirred for half an hour and 12 g (55.77 millimoles) of 3-bromomethyl benzoic acid are added. The reaction mixture is stirred at 50° C. for 3 hours, whereupon it is filtered and the filtrate is evaporated in vacuo. The residue is taken up in 100 ml of ethyl acetate and the suspension is washed with 15 ml of water, 15 ml of a saturated sodium chloride solution, dried over sodium sulfate, filtered and the organic solvent is distilled off in vacuo. Thus 7.3 g of the title compound are obtained, yield 85%.

TLC: $R_f$=0.3 (in a 50:10:1 mixture of benzene, dioxane and acetic acid).

The $R_f$ value of the methyl ester prepared with diazomethane in ether as medium amounts to 0.37 (in a 2:1 mixture of benzene and hexane).

¹H-NMR/CDCl₃, δ/:5.46(s, 2H, CH₂F), 7.28–7.7 (m, 2H, aromatic protons), 7.8–8.3 (m, 2H, aromatic protons).

EXAMPLE 4

Preparation of 3-cyanomethyl-benzoic acid 10 g (43.66 millimoles) of methyl-3-bromomethyl-benzoate are dissolved in 50 ml of anhydrous acetone, whereupon 3.2 g (65.5 millimoles) of sodium cyanide (dried at 105° C.) and 0.327 g (2.18 millimoles) of sodium iodide are added. The reaction mixture is refluxed for 10 hours, cooled and carefully filtered. The acetone is distilled off in vacuo. The crude residue is suspended in 120 ml of ethyl acetate and the suspension is washed twice with 20 ml of water each. The organic solvent is distilled off in vacuo, the residue is dissolved in 20 ml of methanol and a solution of 5.24 g of sodium hydroxide and 20 ml of water is added. The reaction mixture is stirred at room temperature overnight. The methanol is distilled off in vacuo, the residue is diluted with 20 ml water and 20 ml of a saturated sodium chloride solution and the mixture is acidified with a 2N aqueous sodium hydrogen sulfate solution to pH=1–2. The mixture is extracted three times with 60 ml of ethyl acetate each. The organic extract is dried, filtered and the solvent is evaporated in vacuo. The residual crude product is used for the halogenation reaction according to Example 5. (Yield: 5.62 g/80%, crude product)

Analytical data: TLC: $R_f$=0.3 (1:1 mixture of benzene and ethyl acetate).

EXAMPLE 5

Preparation of 3-(bromo-fluoro-methyl)benzoic acid 11,3 g (73.4 millimoles) of 3-fluoromethyl-benzoic acid are dissolved in 75 ml of anhydrous carbon tetrachloride, whereupon 0.2 g of 2,2'-azo-bis-(2-methyl propionitrile) and 13.72 g (77,07 millimoles) of N-bromo-succinimide are added. The reaction mixture is refluxed for 30 minutes. The succinimide formed is removed by filtering the warm mixture. The filtrate is washed with 15 ml of water, dried over sodium sulfate, filtered and the filtrate is evaporated in vacuo. The residual crude product is recrystallized from a fivefold amount of carbon tetrachloride. Thus 13.65 g of the title compound are obtained, yield 79.5%.

Analytical data: TLC: $R_f$=0.3 (50:10:1 mixture of benzene, dioxane and acetic acid). ¹H-NMR/CDCl₃, δ/:6.7 (s, H, CHBrF) 7.45–7.8 (m, 2H, aromatic protons), 7.9–8.4 (m, 2H, aromatic protons).

In an analogous manner to the above process the following compounds are prepared:
3-(fluoro-cyano-methyl)-benzoic acid, $R_f$=0.25 (a 50:10:1 mixture of benzene, dioxane and acetic acid);
3-(fluoro-methoxy-methyl)-benzoic acid, $R_f$=0.32 (a 50:10:1 mixture of benzene, dioxane and acetic acid).

EXAMPLE 6

Preparation of triphenyl-(3-carboxy-4-nitro-benzyl)-phosphonium bromide

A mixture of 15 g (57.7 millimoles) of 3-bromomethyl-6-nitro-benzoic acid, 15.17 g (57.7 millimoles) of triphenyl phosphine and 70 ml anhydrous toluene is refluxed for 2 hours. The precipitated product is filtered off, washed with ether and dried. Thus 21.15 g of the title compound are obtained, yield 71%.

Analytical data: ¹H-NMR/CDCl₃, δ(:5.45/d, 2H, CH₂P⁺, J=16 Hz), 7.5–7.8 (m, 3H, aromatic protons).

In an analogous manner to the above process the following compounds are prepared:
triphenyl-(3 carboxy-benzyl)-phosphonium-bromide, ¹H-NMR/DMSO-d₆, δ(:5,28/d, 2H, CH₂P⁺, J=16 Hz);
triphenyl-[(3-carboxy-phenyl)-cyano-methyl]-phosphonium-bromide, ¹H-NMR/DMSO-d₆, δ(:6.05–6.8 (m, H, CHCN) 7.5–9.05 (m, 4H, aromatic protons);
triphenyl-(3-carboxy-4-chloro-benzyl)-phosphonium-bromide, $R_f$=0.6 (a 5:5:1 mixture of methanol, water and acetic acid);
triphenyl-(2-fluoro-5-carboxy-benzyl)-phosphonium-bromide, $R_f$=0.61 (a 5:5:1 mixture of methanol, water and acetic acid);
triphenyl-(3-carboxy-4-cyano-benzyl/-phosphonium-bromide, $R_f$=0.55 (a 5:5:1 mixture of methanol, water and acetic acid);
triphenyl-/2-hydroxy-3-carboxy-benzyl/-phosphonium-bromide, $R_f$=0.5 (a 5:5:1 mixture of methanol, water and acetic acid).

EXAMPLE 7

Preparation of triphenyl-[(3-carboxy-phenyl)-fluoro-methyl]-phosphonium bromide

A sodium-methyl-sulfenyl-methide (dimesyl sodium) solution is prepared by admixing 15 ml of anhydrous dimethyl sulfoxide with 0.151 g of sodium hydride (J. am. Chem. Soc. 1965, 87, 1345). To this solution under nitrogen at 20° C. 1.5 g (3.13 millimoles) of solid triphenyl-(3-carboxy-benzyl/-phosphonium bromide) dried in vacuo at 80°–90° C. are added. Into the dark-red solution thus obtained perchloryl fluoride is bubbled at room temperature until the red color of the solution disappears and the pH becomes approximately neutral. To the reaction mixture 30 ml of water are added, the pH is adjusted to 1–2 by adding 2N sodium hydrogen sulfate, the mixture is successively extracted three times with 20 ml methylene chloride each and twice with 25 ml of ethyl acetate each, the organic phases are united dried, filtered and the solvent is distilled off in vacuo. The crude product thus obtained may be recrystallized from a mixture of ethanol and ethyl acetate, if necessary. Thus 0.91 g of the title compound are obtained, yield 70%.

Analytical data: TLC: $R_f$=0.6 (a 5:5:1 mixture of methanol, water and acetic acid). ¹H-NMR (DMSO-d₆, δ): 7.25–8.0 (m, 19H, aromatic protons) 6.0–6.9 (d, H, CHF).

EXAMPLE 8

Preparation of 3-(m-chloro-phenoxy)-acetonyl-phosphorane

From 5.75 g (0.25 mole) of metallic sodium and 200 ml of methanol sodium methylate is prepared. 32 g (0.25 mole) of m-chloro-phenol are added, the mixture is refluxed for an hour and evaporated to dryness. The solid residue is suspended in 200 ml of benzene and 88 g (0.25 mole) of chloro acetonyl phosphorane are added. The reaction mixture is refluxed for 3 hours. The sodium chloride is removed by filtration of the hot mixture and the benzene filtrate is evaporated in vacuo. The residual solid crude product is rubbed with 50 ml of ether and the crystals formed are filtered and dried.

Thus 97 g of the crystalline title compound are obtained, yield 87.2%.

Analytical data: mp.: 240°–242° C., TLC: $R_f$=0.5 (a 3:1 mixture of acetone and ethyl acetate). $^1$H-NMR (DCDl$_3$, δ): 7.25–7.9 (m, 19H, aromatic protons), 4.26 (d, =CH—), 4.02 (s, —O—CH$_2$).

IR: 3350, 1590, 1523, 1405, 1240, 1100, 1045, 890, 860, 740, 705, 690 cm$^{-1}$.

In an analogous manner to the above process the following compounds are prepared:

3-propargyloxy-acetonyl-phosphorane $^1$H-NMR (CDCl$_3$, δ): 7.3–7.85 (m, 15H, aromatic protons) 4.3(d, 2H, CH$_2$—C≡), 4.08 (s, 2H, CH$_2$—O), 4.0 (m, 1H, CH=P), 2.42 (t, 1H, ≡CH).

3-(2-methoxy-ethoxy)-acetonyl-phosphorane, $R_f$=0.4 (a 3:1 mixture of acetone and ethyl acetate);

3-crotyloxy-acetonyl-phosphorane, $R_f$=0.51 (a 3:1 mixture of acetone and ethyl acetate);

3-(2,2,2-trifluoro-ethoxy)-acetonyl-phosphorane, $R_f$=0.52 (a 3:1 mixture of acetone and ethyl acetate).

EXAMPLE 9

Preparation of triphenyl-(3,4-didehydro-hexanoyl)-methylene-phosphorane

A 0.5 molar suspension of an ethyl acetylene lithium salt in liquid ammonia (Preparative acetylenic chemistry, L. Brandsma, Elsevier Publishing Company, 1971, page 23) is prepared. To this suspension at −33° C. a solution of 166.75 g of triphenyl-chloro-acetonyl-phosphorane in 100 ml tetrahydrofuran is added so that the solution of triphenyl-chloro-acetonyl-phosphorane is introduced under the surface of liquid ammonia. The mixture is stirred for an hour, and the ammonia is allowed to evaporate. The residual solid residue is dissolved in 300 ml of methylene chloride, the suspension is washed with water, dried over anhydrous sodium sulfate, filtered and the solvent is distilled off in vacuo. The residue is crystallized by rubbing with petrolether. Thus 134.4 g of the title compound are obtained, yield 70%.

Analytical data: TLC: $R_f$=0.61 (a 3:1 mixture of acetone and ethyl acetate).

In an analogous manner to the above process the following compounds are prepared:

triphenyl-(3,4-didehydro-5-methoxy-pentanoyl)-methylene-phosphorane, $R_f$=0.55 (a 3:1 mixture of acetone and ethyl acetate);

triphenyl-(3,4-didehydro-octanoyl)-methylene-phosphorane, $R_f$=0.60 (a 3:1 mixture of acetone and ethyl acetate).

EXAMPLE 10

Preparation of dimethyl-(2-oxo-5-heptyne-1-yl)-phosphonate 20 g (12.9 millimoles) of dimethyl acetonyl phosphonate are dissolved in 100 ml of anhydrous tetrahydrofuran and the solution is cooled to −78° C. To the cooled solution 23.1 g (129 millimoles) of hexamethyl-phosphoric acid triamide are added, whereupon a 12.9 ml of a butyl lithium solution in hexane (concentration 2 millimoles/ml) are added at −78° C. The reaction mixture is stirred at this temperature for half an hour, whereupon a solution of 17.15 g of 1-bromo-2-butyne and 5 ml of tetrahydrofurane is added. The reaction mixture is stirred at a temperature between −60° C. und −70° C. for a further hour, 20 ml of a saturated sodium chloride solution are added and the reaction mixture is allowed to warm to room temperature. The reaction mixture is diluted with 50 ml of water and 50 ml of ether. The phases are separated, the aqueous layer is extracted three times with 30 ml of ether each. The organic phases are united, washed with 15 ml of a saturated sodium chloride solution, dried over anhydrous sodium sulfate, filtered and the solvent is distilled off in vacuo. Thus 22 g of the title compound are obtained, yield 82.5%.

Analytical data: $^1$H-NMR (CDCl$_3$, δ): 3.88 (d, 15 Hz, CH$_3$O), 3.1 (d, 2H, CH$_2$P), 1.85 (t, CH$_3$).

In an analogous manner to the above process the following compound is prepared:

dimethyl-(2-oxo-5-heptyn-1-yl)-phosphonate, $^1$H-NMR (CDCl$_3$, δ): 3.88 (d, CH$_3$O, 15 Hz), 3.1 (d, 2H, CH$_2$P), 1.6 (d, CH$_3$).

EXAMPLE 11

Preparation of 3,3aβ,4,5,6,6aβ-hexahydro-2-oxo-4β-[4-(m-chloro-phenoxy)-3-oxo-1-trans-butenyl]-5α-(p-phenyl-benzoyloxy)-2H-cyclopenta(b)furane 20 g (53,9 millimoles) of 3,3aβ,4,5,6,6aβ-hexahydro-2-oxo-4β-formyl-5α-(p-phenyl-benzoyloxy)-2H-cyclopenta(b)furane (the preparation of this compound is described in Prostaglandins 1977, 14(1), 78–79) are dissolved in 20 ml of anhydrous dichloro methane. To this solution 24,0 g (53.9 millimoles) of solid triphenyl-(m-chloro-phenoxy)-acetonyl-phosphorane and 0.65 g of benzoic acid are added. The reaction mixture is stirred at room temperature for 8 hours, whereupon it is diluted with 100 ml of dichloro methane and washed twice with 10 ml of 1N hydrochloric acid each. The organic layer is dried over anhydrous magnesium sulfate, filtered off and the solvent is removed in vacuo. The crude product is subjected to column chromatography and eluted with 3:1 and 4:1 mixtures of benzene and ethyl acetate. The fractions corresponding to an $R_f$ value of 0.26 are pooled. The solvent is distilled off in vacuo. Thus 21.48 g of the title compound are obtained, yield 77%. The product can be recrystallized from anhydrous ethanol.

Analytical data: TLC: $R_f$=0.26 (a 4:1 mixture of benzene and ethyl acetate). $^1$H-NMR (CDCl$_3$, δ): 6.4–8.15 (m, 11H, aromatic protons and enone CH—CH= dd and enone =CH—CO d signs), 5.12 (m, 6a H), 5.37 (q, H-5), 4.7 (s, —CH$_2$—O).

In an analogous manner to the above process 3,3aβ,4,5,6,6aβ-hexahydro-2-oxo-4β-(3-oxo-1-trans-nonenyl(-5α-)p-phenyl-benzoyloxy)-2H-cyclopenta(b)furane is prepared.

EXAMPLE 12

Preparation of 3,3aβ,4,5,6,6aβ-hexahydro-2-hydroxy-4β-(3S-hydroxy-1-trans-nonenyl)-5α-hydroxy-2H-cyclopenta(b)furane 63.7 g of (0.117 mole) of 3.3aβ,4,5,6,6aβ-hexahydro-2-oxo-4β-(3-oxo-1-trans-nonenyl)-5α-(p-phenyl-benzoyloxy)-2H-cyclopenta(b)furane are dissolved in 200 ml of anhydrous ethanol. The solution is cooled to −20° C. and 240 ml of a 0.5 molar ethanolic sodium borohydride solution is added. The reaction mixture is stirred at a temperature between −20° C. and −25° C. for 30 minutes, whereupon it is poured into 500 ml of N hydrochloric acid and the mixture thus obtained is extracted four times with 100 ml of ethyl acetate each. The organic phases are united, dried over sodium sulfate, filtered and the solvent is distilled off in vacuo. The crude product thus obtained is subjected to column chromatography on silicagel and eluted with a 1:1 mixture of ethyl acetate and benzene. From the two isomers the less polar isomer corresponds to the "S" configuration and shows an $R_f$ value of 0.33 (in a 1:1 mixture of benzene and ethyl acetate).

The fractions corresponding to the $R_f$ values of 0.33 and 0.28, respectively are separately pooled and evaporated. Thus 25.6 g of the less polar "S" allyl alcohol and 23.2 g of the polar "R" allyl alcohol are obtained.

The product containing 25.6 g of the less polar "S" allyl alcohol is dissolved in 130 ml of anhydrous tetrahydrofuran and the solution is cooled to −78° C. on a dry-ice acetone bath. To this solution 45.5 ml of a diisobutyl aluminium hydride solution formed in hexane (concentration 2.28 millimoles)ml) are added dropwise under inert gas atmosphere at such a rate that the temperature should not exceed −60° C. The addition having been completed the reaction mixture is stirred for 30 minutes, 50 ml of a 2N aqueous sodium hydrogen sulfate solution is added and the temperature is allowed to rise to room temperature. The mixture is then acidified to pH 1-2 and 300 ml of ethyl acetate are added. The layers are separated, the aqueous phase is extracted three times with 20 ml of ethyl acetate each, the organic layers are united, dried, filtered and evaporated in vacuo. Thus 24.8 g of a bicyclic lactol product are obtained ($R_f$=0,45, a 3:1 mixture of ethyl acetate and benzene). In order to split off the p-phenyl-benzoyl protecting group, the said product is dissolved in 100 ml of anhydrous methanol and 6.53 g (0.047 mole) of anhydrous potassium carbonate are added.

The suspension is stirred for half an hour, the reaction mixture is filtered, the solvent is distilled off in vacuo. The crude product thus obtained is purified by column chromatography on a silicagel G column and eluted with ethyl acetate. The fractions corresponding to an $R_f$ value of 0.28 are pooled and evaporated in vacuo. Thus 9.44 g of the title compound are obtained. Yield 71% (related to the "S" alcohol").

Analytical data: TLC: $R_f$=0.28 (ethyl acetate), $R_f$=0.3 (a 20:10:1 mixture of benzene, dioxane and acetic acid).

In an analogous manner to the above process the following compounds are prepared:

3,3a$\beta$,4,5,6,6a$\beta$-hexahydro-2-hydroxy-4$\beta$-(3S-hydroxy-1-trans-decenyl)-5$\alpha$-hydroxy-2H-cyclopenta(b)furan, $R_f$=0.3 (a 20:10:1 mixture benzene, dioxane and acetic acid);

3,3a$\beta$,4,5,6,6a$\beta$-hexahydro-2-hydroxy-4$\beta$-[3S-hydroxy-4-(m-chloro-phenoxy)-1-trans-butenyl]-5$\alpha$-hydroxy-2H-cyclopenta(b)furane, $R_f$=0.23 (ethyl acetate);

3,3a$\beta$,4,5,6,6a$\beta$-hexahydro-2-hydroxy-4$\beta$-(3S-hydroxy-4-methoxy-ethoxy-1-trans-butenyl)-5$\alpha$-hydroxy-2H-cyclopenta(b)furan, $R_f$=0.26 (a 20:10:1 mixture of benzene, dioxane and acetic acid);

3.3a$\beta$4,5,6,6a$\beta$-hexahydro-2-hydroxy-4$\beta$-(3S-hydroxy-1-trans-6,7-didehydro-octenyl)-5$\alpha$-hydroxy-2H-cyclopenta(b)furan, $R_f$=0.27 (ethyl acetate).

EXAMPLE 13

Preparation of
3,3a$\beta$,4,5,6,6a$\beta$-hexahydro-2-hydroxy-4$\beta$-(3S-hydroxy-1-decinyl)-5$\alpha$-hydroxy-2H-cyclopenta(b)furan 55.9 g (0,1 mole) of 3.3a$\beta$,4,5,6,6a$\beta$-hexahydro-2-oxo-4$\beta$-(3-oxo-1-trans-decenyl)-5$\alpha$-(p-phenyl-benzoyloxy)-2H-cyclopenta(b)furan are dissolved in 200 ml of anhydrous dichloro methane and at room temperature 6.6 ml of bromine are added dropwise and thereafter 25.6 ml (0.3 mole) of pyridine are added. The reaction mixture is refluxed for 3 hours, whereupon 100 ml of methylene chloride are added, the mixture is washed with 50 ml of 1N hydrochloric acid and the aqueous phase is extracted twice with 75 ml of methylene chloride each. The organic layers are united and washed with 50 ml of a 5% aqueous sodium hydrogen carbonate solution, dried, filtered and evaporated in vacuo. Thus 64 g of a crude product are obtained ($R_f$=0,3, a 4:1 mixture of benzene and ethyl acetate). The crude product is dissolved in 200 ml of anhydrous ethanol. The solution is cooled to −20° C. and 198 ml of a 0.5 molar ethanolic sodium borohydride solution are added. The reaction mixture is stirred at a temperature between −20° C. and −25° C. for 30 minutes, whereupon it is poured into 500 ml of 0.1N hydrochloric acid and the mixture is extracted four times with 100 ml of ethyl acetate each. The organic layers are united, dried over sodium sulfate, filtered and the solvent is distilled off in vacuo. The crude product thus obtained is subjected to column chromatography on silicagel and diluted with a 3:2 mixture of benzene and ethyl acetate.

From the two isomers formed the less polar isomer ($R_f$=0.2, a 3:1 mixture of benzene and ethyl acetate) has "S" configuration. The fractions corresponding to the $R_f$ values 0.2 and 0.13 respectively, are separately pooled and the solvent is removed in vacuo. Thus 26.1 g (40%) of the less polar "S" allyl alcohol and 25 g of the polar "R" allyl alcohol are obtained.

26.1 g of the less polar "S" allyl alcohol are dissolved in 150 ml of anhydrous tetrahydrofuran and the solution is cooled on a dry-ice acetone bath to −78° C. To the solution in an inert gas atmosphere and at −78° C. 17.55 ml of a diisobutyl aluminium hydride solution formed with hexane are added dropwise (concentration 2.28 millimoles/ml) at such a rate that the temperature should not exceed −60° C. The addition having been terminated the reaction mixture is stirred for 30 minutes whereupon 20 ml of a 2N aqueous sodium hydrogen sulfate solution are added and the temperature is allowed to rise to room temperature. The pH is adjusted to an acidic value between 1 and 2,300 ml of ethyl acetate are added. The phases are separated, the aqueous layer is extracted three times with 20 ml of ethyl acetate each. The organic layers are united, dried, filtered and the solvent is distilled off in vacuo. Thus 24.3 g of a bicyclic lactol are obtained ($R_f$=0.15, a 3:1 mixture of benzene and ethyl acetate). In order to remove the p-phenyl-benzoyl protecting group this product is dissolved in 100 ml of anhydrous methanol and 5.66 g (0.041 mole) of anhydrous potassium carbonate are added. The suspension is stirred for half an hour, the reaction mixture is filtered and the solvent is removed in vacuo. The crude product thus obtained is purified by column chromatography on silicagel G and eluted with ethyl acetate. The fractions corresponding to an $R_f$ value of 0.25 are pooled and the solvent is distilled off in vacuo. Thus 10.48 g of the bromovinyl lactol are obtained; yield 73.5% (related to the "S" alcohol).

Analytical data: TLC: $R_f$=0.25 (ethyl acetate) $^1$H-NMR (CDCl$_3$, $\delta$): 5.8 (d, 1H, C$\underline{H}$=CBr), 5.5-5.75 (m, 1H, OC$\underline{H}$OH), 3.85-4.8 (m, 3H, C$\underline{H}$O), 0.85 (d)t, 3H C$\underline{H}_3$).

10.48 g of the above bromovinyl lactol are dissolved in 50 ml of anhydrous dimethyl sulfoxide and at room temperature 3.12 g (0.027 mole) of potassium tertiary butoxide are added. The suspension is stirred at room temperature for 30 minutes, diluted with 300 ml of ethyl acetate, the organic layer is separated and washed three times with 100 ml and twice with 50 ml of water each. The united organic layers are dried, filtered and evaporated in vacuo. The crude product is purified by column chromatography on silicagel and eluted with a 4:1 mixture of ethyl acetate and acetone. The fractions corresponding to an $R_f$ value of 0.33 (ethyl acetate) are pooled and the solvent is distilled off in vacuo. Thus 6.22 g of the title compound are obtained.

Analytical data: TLC: $R_f=0.33$ (ethyl acetate). $^1$H-NMR (CDCl$_3$, δ): 5.4–5.8 (m, 1H, OC$\underline{H}$OH), 3.8–4.8 (m, 3H, C$\underline{H}$O), 0.084-(d)t, 3H, C$\underline{H}_3$).

EXAMPLE 14

Preparation of 2,3,4,17,18,19,20-heptanor-1,5-inter-m-phenylene-13,14-didehydro-16-(methoxy-ethoxy)-PGF$_{2\alpha}$-methyl ester 28.6 g (0.06 mole) of dry triphenyl-(3-carboxy-benzyl)-phosphonium bromide are weighed in a 150 ml round-bottomed flask, whereupon 58 ml of a sodium methyl sulfenyl methide solution formed with dimethyl sulfoxide (concentration 2 millimoles/ml, J. Am. Chem. Soc. 1965, 87, 1345) are added dropwise under nitrogen atmosphere under stirring and cooling. The red phosphorane solution thus obtained is stirred at room temperature for 30 minutes and diluted with 5 ml of dimethyl sulfoxide. Thus 5.72 g (0.02 mole) of 3,3aβ,4,5,6-,6aβ-hexahydro-2-hydroxy-4β-[3S-hydroxy-4-(methoxyethoxy)-1-butynyl]-5α-hydroxy-2H-cyclopenta(b)furan are obtained.

The reaction mixture is stirred at 40° C. for 2 hours, whereupon it is poured into a mixture of 30 g of ice and 100 ml of water, and the pH is adjusted to 3–4 by adding a 1N aqueous sodium hydrogen sulfate solution. The solution is extracted four times with 30 ml of ethyl acetate each.

The united organic solutions are extracted three times with 16 ml of 1N sodium hydroxide solution each. The united alkaline extracts are acidified to a pH value of 3.5–4 by adding a 1N sodium hydrogen sulfate solution, 80 ml of diethyl ether and thereafter 10 ml of a 1 molar etheral diazomethane solution are added. The ether phase is separated, washed with a saturated sodium chloride solution, dried and the solvent is removed in vacuo. Thus 5.6 g of a crude product are obtained which is subjected to column chromatography on silicagel and eluted with a 3:1 mixture of ethyl acetate and benzene. The fractions corresponding to an $R_f$ value of 0.23 are pooled and evaporated. Thus 5 g of the title compound are obtained, yield 60%.

Analytical data: TLC: $R_f=0.23$ (a 3:1 mixture of ethyl acetate and benzene). $^1$H-NMR (CDCl$_3$,): 7.3–8.1 (m, 4H, aromatic protons), 6.2–6.7 (m, 2H, trans H-5, H-6), 5.7–5.95 (m, 2H, cis H-5, H-6), 4.0–4.35 (m, 3H, H-9, H-11, H-15), 3.92 (s, 3H, C$\underline{H}_3$O(ester), 3.65 (s, 3H, C$\underline{H}_3$O ether).

In an analogous manner to the above process the following compounds are prepared:

2,3,4,17,18,19,20-heptanor-1,5-inter-m-phenylene-5-fluoro-16-(m-chloro-phenoxy)-PGF$_{2\alpha}$-methyl ester, $R_f=0.3$ (a 20:10:1 mixture of benzene, dioxane and acetic acid);

2,3,4,17,18,19,20-heptanor-1,5-inter-m-phenylene-16-propargyloxy-PGF$_{2\alpha}$-methyl ester, $R_f=0.36$ (a 20:10:1 mixture of benzene, dioxane and acetic acid);

2,3,4,17,18,19,20-heptanor-1,5-inter-m-phenylene-16-crotyloxy-PGF$_{2\alpha}$-methyl ester, $R_f=0.39$ (a 20:10:1 mixture of benzene, dioxane and acetic acid);

2,3,4,17,18,19,20-heptanor-1,5-inter-m-phenylene-16-(2,2,2-trifluoroethoxy)-PGF$_{2\alpha}$-methyl ester, $R_f=0.27$ (a 20:10:1 mixture of benzene, dioxane and acetic acid);

2,3,4-trinor-1,5-inter-m-phenylene-17,18-didehydro-PGF$_{2\alpha}$-methyl ester, $R_f=0.41$ (a 20:10:1 mixture of benzene, dioxane and acetic acid);

2,3,4-trinor-1,5-inter-m-phenylene-$\Delta^{18}$-PGF$_{2\alpha}$-methyl ester, $R_f=0.59$ (a 20:20:1 mixture of benzene, dioxane and acetic acid);

2,3,4-trinor-1,5-inter-m-phenylene-5-cyano-20-methyl-PGF$_{2\alpha}$-methyl ester, $R_f=0.4$ (a 20:10:1 mixture of benzene, dioxane and acetic acid);

2,3,4-trinor-1,5-inter-m-phenylene-14-bromo-17,18-didehydro-20-ethyl-PGF$_{2\alpha}$-methyl ester, $R_f=0.6$ (a 20:10:1 mixture of benzene, dioxane and acetic acid);

2,3,4-trinor-1,5-inter-m-phenylene-13,14-17,18-bis-didehydro-PGF$_{2\alpha}$-methyl ester, $R_f$ 2 0.60 (a 20:20:1 mixture of benzene, dioxane and acetic acid);

2,3,4-trinor-1,5-inter-m-phenylene-13,14-didehydro-$\Delta^{18}$-PGF$_{2\alpha}$-methyl ester, $R_f=0.6$ (a 20:20:1 mixture of benzene, dioxane and acetic acid).

EXAMPLE 15

Preparation of 2,3,4-trinor-1,5-inter-m-phenylene-13,14-didehydro-PGF$_{2\alpha}$-amide 2.5 g (6.3 millimoles) of 2,3,4-trinor-1,5-inter-m-phenylene-13,14-didehydro-20-ethyl-PGF$_{2\alpha}$-methyl ester are dissolved in 36 ml of methanol, whereupon a solution of 1.26 g (31.5 millimoles) of sodium hydroxide and 12 ml of water are added. The reaction mixture is allowed to stand overnight whereupon the methanol is distilled off in vacuo. To the residue 10 ml of water and 10 ml a saturated sodium chloride solution are added, the pH is adjusted to 2 and the aqueous phase is extracted five times with 20 ml of ethyl acetate each. The organic layers are united, filtered and the solvent is distilled off in vacuo.

The free carboxylic acid thus obtained (2.5 g) is dissolved in 20 ml of anhydrous methylene chloride, 1.3 g (12.6 millimoles) of triethyl amine and 860 mg (6.3 millimoles) of chloro isobutyl formiate are added. The mixture is stirred at room temperature for half an hour, whereupon at −5° C. 30 ml of acetonitrile saturated with ammonia are added and the mixture is stirred at 10° C. for a further period of 10 minutes. The reaction mixture is diluted with 50 ml of a saturated sodium chloride solution and 10 ml of water. The mixture thus formed is extracted five times with ethyl acetate 20 ml each. The organic layers are united, washed twice with 20 ml of 2N hydrochloric acid each, twice with 20 ml of 5% aqueous sodium hydrogen carbonate solution each and 20 ml of saturated aqueous sodium chloride solution, dried over sodium sulfate, filtered and the solvent is distilled off in vacuo. The crude product is subjected to column chromatography on silicagel and eluted with a 3:1 mixture of acetone and ethyl acetate. The fractions corresponding to an $R_f$ value of 0.25 (a 20:20:1 mixture of benzene, dioxane and ethyl acetate) are pooled and evaporated in vacuo. Thus 2.24 g of the title compound are obtained, yield 93%.

Analytical data: $R_f=0.25$ (a 20:20:1 mixture of benzene, dioxane and acetic acid).

EXAMPLE 16

Preparation of 2-decarboxy-2-cyano-2,3,4-trinor-1,5-inter-m-phenylene-13,14-didehydro-20-ethyl-PGF$_{2\alpha}$ 4 g (9.64 millimoles) of 2,3,4-trinor-1.5-inter-m-phenylene-13,14-didehydro-20-ethyl-PGF$_{2\alpha}$-amide are dissolved in 40 ml of anhydrous dimethyl formamide, whereupon 7.27 g (48 millimoles) of dimethyl-tertiary butyl-sylyl chloride and 7.9 g (115 millimoles) of imidazole are added. The mixture is stirred at room temperature overnight, whereupon 400 ml of a 1:1 mixture of petrolether and ether are added. The organic layer is washed three times with 50 ml of water and 50 ml of a saturated sodium chloride solution each, dried, filtered and evaporated in vacuo. The tris-sylyl compound thus obtained (10 g) is dissolved in 40 ml of pyridine and at room temperature 2.2 g (10.6 millimoles) of N,N'-dicyclohexyl-carbodiimide are added. The reaction mixture is diluted with 250 ml of ether. The precipitated dicyclohexyl carbodiimide is filtered off and the filtrate is evaporated in vacuo. The residue is suspended in 116 ml of a molar tetra-n-butyl-ammonium fluoride solution formed with tetrahydrofurane and the mixture is stirred for 2 days. To the reaction mixture 300 ml of ethyl acetate are added, the mixture is washed three times with 40 ml of water each and 50 ml of a saturated sodium chloride solution, dried and evaporated in vacuo. Thus 2.6 g of the title compound are obtained, yield: 68%.

Analytical data: TLC: $R_f=0.3$ (a 20:10:1 mixture of benzene, dioxane and acetic acid). $^1$H-NMR/CDCl$_3$, $\delta$(:0.85)t, 3H, CH$_3$), 5.45–6.5 (m, 2H, olephinic protons), 7.2–8.1 (m, 4H, aromatic protons).

EXAMPLE 17

Preparation of 2-decarboxy-2-(1H-tetrazole-5-yl)-2,3,4-trinor-1,5-inter-m-phenylene-13,14-didehydro-20-ethyl-PGF$_2$ One proceeds as described in Example 16 except that in the place of the use of the tetra-n-butyl-ammonium-fluoride the product is dissolved in 50 ml of dimethyl formamide and 1.22 g (19.3 millimole) of sodium azide and 5.15 g of ammonium chloride are added. The reaction mixture is heated at 110°–120° C. for 3 hours whereupon it is cooled back to room temperature, diluted with 100 ml of chloroform, washed twice with 200 ml of water each, dried over sodium sulfate, filtered and the organic solvent is distilled off in vacuo. The residue is suspended in 20 ml of anhydrous tetrahydrofuran and 116 ml of tetrabutyl-ammonium fluoride are added. The mixture is stirred at room temperature for 3 hours, diluted with 100 ml of chloroform, washed three times with 10 ml of water each, dried, filtered and evaporated in vacuo. Thus 2.7 g of the title compound are obtained, yield 65%.

Analytical data: TLC: $R_f=0.03$ (a 20:10:1 mixture of benzene, dioxane and acetic acid).

EXAMPLE 18

Preparation of 2,3,4-trinor-1,5-inter-m-phenylene-13,14-didehydro-20-ethyl-PGF$_{2\alpha}$-methane sulfonamide From 2,3,4-trinor-1,5-inter-m-phenylene-13,14-didehydro-20-ethyl-PGF$_{2\alpha}$-methyl ester a mixed anhydride is prepared with chloro isobutyl formiate according to the process described in Example 15. The solution of the said mixed anhydride and 10 ml of anhydrous dimethyl formamide is added to the sodium salt of methane sulphonamide, prepared by reacting 2.8 g of methane-sulphonamide with 1.36 g of sodium ethylate; the sodium salt is previously made free of methanol with the aid of benzene.

To the mixture 2 ml of hexamethyl phosphoric acid triamide is added and the mixture is stirred at this temperature for 24 hours. The reaction mixture is acidified with a cold 1 molar sodium hydrogen sulfate solution to pH 3 and extracted three times with 30 ml of ethyl acetate each. The organic extracts are united, washed with water, dried, filtered and evaporated in vacuo. Thus 2.25 g of the title compound are obtained, yield 75%.

Analytical data: TLC: $R_f=0.05$ (in a 20:10:1 mixture of toluene, dioxane and acetic acid).

EXAMPLE 19

Preparation of 2,3,4-trinor-1,5-inter-m-phenylene-5-iodo-13,14-18,19-bis-didehydro-20-ethyl-PGI$_1$-methyl ester 2.2 g (5.13 millimoles) of 2,3,4-trinor-1,5-inter-m-phenylene-13,14-18,19-bis-didehydro-20-ethyl-PGF$_{2\alpha}$-methyl ester are dissolved in 10 ml of methylene chloride, whereupon 52 ml (52 millimoles) of a sodium hydrogen carbonate solution (concentration 1 millimole/ml) are added under stirring. 103 ml of a iodine solution formed with methylene chloride (concentration 0.1 millimole/ml) are added to the two-phase system thus obtained. The reaction mixture is intensively stirred at room temperature for an hour, diluted with 300 ml of ethyl acetate, the excess of iodine is decomposed by reduction with a 5% sodium thiosulfate solution. The organic phase is separated and the aqueous layer is extracted twice with 25 ml of ethyl acetate each. The organic layers are united, washed with a saturated sodium chloride solution, dried over anhydrous sodium sulfate filtered and the solvent is distilled off in vacuo. Thus 2.9 g of the title compound are obtained.

Analytical data: TLC: $R_f=0.65$ and 0.58 (a 3:1 mixture of ethyl acetate and benzene).

EXAMPLE 20

Preparation of 2,3,4-trinor-1,5-inter-m-phenylene-5-bromo-16-fluoro-13,14-didehydro-20-ethyl-PGI$_1$-methyl ester 470 mlg (1.1 millimole) of 2,3,4-trinor-1,5-inter-m-phenylene-16-fluoro-13,14-didehydro-20-ethyl-PGF$_{2\alpha}$-methyl ester are dissolved in 5 ml of a 1:1 mixture of anhydrous chloroform and tetrahydrofurane. The solution is cooled to −78° C. (with a cooling mixture of dry ice and acetone) and stirred under inert gas. In one portion 215.4 g of solid N-bromo-succinimide are added. The reaction mixture is stirred at −78° C. for 10 minutes, the cooling bath is removed and the temperature of the mixture is allowed to rise to room temperature. The mixture is stirred at this temperature for 30 minutes, diluted with 50 ml of chloroform and washed three times with 20 ml of water each. The organic layer is dried over sodium sulfate, filtered and the solvent is distilled off in vacuo. Thus 560 mg of the title compound are obtained.

Analytical data: TLC: $R_f=0.59$ and 0.54 (ethyl acetate).

EXAMPLE 21

Preparation of 2,3,4-trinor-1,5-inter-m-phenylene-5-phenyl-selenyl-15-methyl-13,14-didehydro-20-ethyl-PGI$_1$-methyl ester One proceeds according to Example 20 except that the N-bromo-succinimide is replaced by 1.21 ml of a phenyl selenyl chloride solution formed with methylene chloride (concentration 1.21 millimoles/ml). Thus 650 mg of the title compound are obtained.

Analytical data: TLC: $R_f=0.62$ and 0.57 (ethyl acetate).

EXAMPLE 22

Preparation of 2,3,4-trinor-1,5-inter-m-phenylene-13,14-didehydro-15-methyl-16-fluoro-20-ethyl-PGI$_2$-methyl ester To 471 mg (0.85 millimoles) of 2,3,4-trinor-1,5-inter-m-phenylene-5-iodo-13,14-didehydro-15-methyl-16-fluoro-20-ethyl-PGI$_1$-methyl ester 50 ml of distilled 1,5-diazabicyclo (4.3.0)non-5-en are added. The mixture is stirred at 50° C. for 1 hour and cooled back to room temperature. The reaction mixture is diluted with 100 ml of ether, the organic layers are washed twice with 25 ml of water each, dried over sodium sulfate, filtered and evaporated in vacuo. Thus 390 mg of a crude product are obtained, which is chromatographied on a silicagel column and eluted with a 3:1 mixture of ether and acetone. The fractions corresponding to the $R_f$ value of 0.50 (a 3:1 mixture of benzene and ethyl acetate) are pooled and the solvent is distilled off in vacuo. Thus 300 mg of the title compound are obtained, yield 85%.

Analytical data: TLC: $R_f=0.5$ (a 3:1 mixture of benzene and ehtyl acetate, run twice). $^1$H-NMR (CDCl$_3$, δ): 7.25–8.1 (m, 4H, aromatic protons), 5.95–5.3 (s, 1H, E and Z H-5), 4.05–4.5 (2H, H-11 and H-15), 4.75 (dt, 1H, H-9), 3.95 (3H, ester CH$_3$), 0.85 (t, 3H, CH$_3$).

In an analogous manner to the above process the following compounds are prepared:

2,3,4-trinor-1,5-inter-(4-chloro-1,3-phenylene)-13,14-didehydro-20-ethyl-PGI$_2$-methyl ester, $R_f=0.64$ and 0.60 (ethyl acetate);

2,3,4-trinor-1,5-inter-(4-fluoro-1,3-phenylene)-13,14-didehydro-20-ethyl-PGI$_2$-methyl ester, $R_f=0.64$ and 0.60 (ethyl acetate);

2,3,4-trinor-1,5-inter-(6-cyano-1,3-phenylene)-13,14-didehydro-20-ethyl-PGI$_2$-methyl ester, $R_f=0.49$ and 0.46 (ethyl acetate);

2,3,4-trinor-1,5-inter-(6-nitro-1,3-phenylene)-13,14-didehydro-20-ethyl-PGI$_2$-methyl ester, $R_f=0.53$ and 0.51 (ethyl acetate);

2,3,4-trinor-1,5-inter-(6-acetylamino-1,3-phenylene)-13,14-didehydro-20-ethyl-PGI$_2$-methyl ester, $R_f=0.22$ (a 2:1 mixture of dichloromethane and acetone);

2,3,4-trinor-1,5-inter-(6-hydroxy-1,3-phenylene)-13,14-hidehydro-20-ethyl-PGI$_2$-methyl ester, $R_f=0.34$ (a 2:1 mixture of dichloromethane and acetone);

2,3,4,17,18,19,20-heptanor-1,5-inter-m-phenylene-5-fluoro-13,14-didehydro-16-(3-chloro-phenoxy)-PGI$_2$-methyl ester, $R_f=0.68$ and 0.66 (a 3:1 mixture of dichloromethane and acetone);

2,3,4,17,18,19,20-heptanor-1,5-inter-m-phenylene-13,14-didehydro-16-propargyloxy-PGI$_2$-methyl ester, $R_f=0.55$, 0.51 (a 2:1 mixture of dichloromethane and acetone);

2,3,4,17,18,19,20-heptanor-1,5-inter-m-phenylene-13,14-didehydro-16-crotyloxy-PGI$_2$-methyl ester, $R_f=0.6$ and 0.55 (a 2:1 mixture of dichloromethane and acetone);

2,3,4,17,18,19,20-heptanor-1,5-inter-m-phenylene-13,14-didehydro-16-methoxy-ethoxy-PGI$_2$-methyl ester, $R_f=0.40$ and 0.37 (a 2:1 mixture of dichloromethane and acetone);

2,3,4,17,18,19,20-heptanor-1,5-inter-m-phenylene-13,14-didehydro-16-(2,2,2-trifluoroethoxy)-PGI$_2$-methyl ester, $R_f=0.52$ and 0.48 (a 3:1 mixture of dichloromethane and acetone);

2,3,4,17,18,19,20-heptanor-1,5-inter-m-phenylene-13,14-didehydro-16-(2-butyn-1-yl-oxy)-PGI$_2$-methyl ester, $R_f=0.59$ and 0.56 (a 2:1 mixture of dichloromethane and acetone);

2,3,4-trinor-1,5-inter-m-phenylene-13,14-17,18-bis-didehydro-PGI$_2$-methyl ester, $R_f=0.67$ and 0.62 (a 3:1 mixture of dichloromethane and acetone);

2,3,4-trinor-1,5-inter-m-phenylene-13,14-didehydro-$\Delta^{19}$-20-methyl-PGI$_2$-methyl ester, $R_f=0.69$ and 0.66 (a 3:1 mixture of dichloromethane and acetone);

2,3,4-trinor-1,5-inter-m-phenylene-5-fluoro-13,14-didehydro-PGI$_2$-methyl ester, $R_f=0.6$ and 0.55 (ethyl acetate);

2,3,4-trinor-1,5-inter-m-phenylene-5-methoxy-13,14-didehydro-PGI$_2$-methyl ester, $R_f=0.61$ and 0.58 (a 3:1 mixture of dichloromethane and acetone);

2,3,4-trinor-1,5-inter-m-phenylene-5-cyano-13,14-didehydro-PGI$_2$-methyl ester, $R_f=0.56$ and 0.52 (a 3:1 mixture of dichloromethane and acetone).

EXAMPLE 23

Preparation of 2,3,4-trinor-1,5-inter-m-phenylene-13,14-didehydro-20-ethyl-PGI$_2$-amide 1.8 g (3.16 millimoles) of 2,3,4-trinor-1,5-inter-m-phenylene-5-phenyl-selenyl-13,14-didehydro-20-ethyl-PGI$_1$-amide are dissolved in 20 ml of tetrahydrofurane, whereupon at 0° C. 3,5 ml of 30% hydrogen peroxide are added. The reaction mixture is stirred at 0° C. for an hour, the temperature is allowed to rise to room temperature and the mixture is stirred at room temperature for a further hour. The reaction mixture is diluted with 20 ml of water and 20 ml of a saturated sodium chloride solution and extracted successively three times with 15 ml of ether and three times with 15 ml of ethyl acetate each. The organic layers are united, washed twice with 20 ml of sodium hydrogen carbonate solution each and with 20 ml of water, dried over sodium sulfate, filtered and the solvent is distilled off in vacuo. Thus 957 mg of the title compound are obtained, yield 71.5%.

Analytical data: TLC:$R_f=0.28$ (a 20:20:1 mixture of benzene, dioxane and acetic acid).

EXAMPLE 24

Preparation of
2,3,4-trinor-1,5-inter-m-phenylene-13,14,17,18-bis-didehydro-20-methyl-6a-carbaprostaglandin-$I_2$-methyl ester A solution of 40 millimoles of sodium-methyl-sulfenyl-methide and 40 ml of dimethyl sulfoxide (prepared from 960 mg of sodium hydride and 40 ml of anhydrous dimethyl sulfoxide) is cooled to 15°–20° C., whereupon 9.54 g (20 millimoles) of triphenyl-3-carboxybenzyl-phosphonium-bromide are added. The red solution thus formed is stirred at 35° C. for 30 minutes, cooled back to room temperature and 2.62 g (3 millimoles) of 7α-{tetrahydropyran-2-yl-oxy}-6β-[3S-(tetrahydropyran-2-yl)-oxy-1,4-noninyl]-bicyclo(3.3.0)octan-3-one dissolved in 2 ml of anhydrous tetrahydrofuran are added. The reaction mixture is stirred at 40° C. for 48 hours, the solution is cooled to room temperature and 10 ml of water are added. The pH of the mixture is adjusted to a neutral value by adding a 1N sodium hydrogen sulfate solution and extracted three times with 20 ml of ethyl acetate each. The organic extracts are united, washed three times with 10 ml of water each and with 10 ml of a saturated sodium chloride solution, dried over anhydrous sodium sulfate and dried. The solution is cooled to 0° C. and 10 ml of an ehterous diazomethane solution (concentration 1 millimole/ml) are added. The solvent is distilled off in vacuo and the crude product (4 g) is purified by column chromatography on silicagel and elution with a 4:1 mixture of benzene and ethyl acetate. The fractions corresponding to $R_f$ values of 0.40 and 0.36 (a 3:1 mixture of benzene and ethyl acetate) are pooled and evaporated in vacuo. Thus 1,3 g (yield 38%) of the product corresponding to $R_f=0.40$ and 1.36 g of (yield 40%) of the product corresponding to $R_f=0.38$ are obtained.

The said fractions are dissolved separately in a 3:1:1.5 mixture of acetic acid, water and tetrahydrofuran (20 ml) and stirred at 40° C. for 3 hours. The reaction mixture is cooled to room temperature and 40 ml of a saturated sodium chloride solution and 40 ml of ethyl acetate are added. The organic layer is separated, and the aqueous phase is extracted twice with 5 ml of methyl acetate each. The organic layers are united and washed neutral twice with 10 ml of a saturated sodium hydrogen carbonate solution each. The organic phase is dried over anhydrous sodium sulfate, filtered and evaporated in vacuo. The crude product is purified by column chromatography on silicagel and elution with ethyl acetate. Thus 782.5 g (32%) and 843.5 g (yield 34.5%) of the title compound are obtained, which corresponds to the 5 (Z) and 5 (E) isomers, respectively.

Analytical data: TLC:$R_f=0.20$ and 0.17 (ethyl acetate), $^1$H-NMR(CDCl$_3$,δ):7.15–8.05(m, 4H, aromatic protons) 5.25–5.80 (1H, H-5 E and Z isomers), 3.5–4.3 (5H), 0.87 (3H).

EXAMPLE 25

Preparation of
2,3,4-trinor-1,5-inter-(4-fluoro-1,3-phenylene)-13,14-didehydro-20-ethyl-PGF$_{2\alpha}$ sodium salt 813.5 mg (1.83 millimoles) of 2,3,4-trinor-1,5-inter-(4-fluoro-1,3-phenylene)-13,14-didehydro-20-ethyl-PGF$_{2\alpha}$-methyl ester are dissolved in 1.5 ml of methanol and to the solution 11 ml of a 0.5 methanolic sodium hydroxide solution are added. The mixture is stirred at room temperature overnight and the methanol is distilled off in vacuo. The product is dissolved in 3 ml of water, whereupon 10 ml of a saturated sodium chloride solution and 50 ml of ethyl acetate are added. The mixture is cooled to 0° C. and acidified to pH 4-5 with a molar oxalic acid solution. The phases are separated, the aqueous layer is extracted three times with 20 ml of ethyl acetate each, the organic solutions are united, dried over anhydrous sodium sulfate, filtered and the solvent is distilled off in vacuo. The residual acid is dissolved in 3 ml of methanol and at 0° C. 1.8 ml of a methanolic sodium hydroxide solution (concentration 1 millimole/ml) are added. The methanol is distilled off in vacuo, the residue is suspended in petrolether and the petrolether is decanted. Thus 679.2 mg of the title compound are obtained (yield 82%).

Analytical data: TLC: $R_f=0.46$ (a 20:10:1 mixture of benzene, dioxane and acetic acid). $^1$H-NMR (deutoromethanol, δ:0.9 (t, 3H, CH$_3$), 5.3 (s, H-5 Z isomer), 5.86 (s, H-5, E isomer), 6.7–7.3 (m, 1H, aromatic protons), 7.5–8.15 (m, 2H, aromatic protons).

In an analogous manner to the above process the following compounds are prepared:

2,3,4,17,18,19,20-heptanor-1,5-inter-m-phenylene-5-fluoro-13,14-didehydro-16(3-chloro-phenoxy)-PGI$_2$-dicyclohexylamine salt, $R_f=0.46$ and 0.44 (a 20:10:1 mixture of benzene, dioxane and acetic acid);

2,3,4,17,18,19,20-heptanor-1,5-inter-m-phenylene-13,14-didehydro-16-crotyloxy-PGI$_2$-tetrabutyl-ammonium salt, $R_f=0.49$ and 0.43 (a 20:10:1 mixture of benzene, dioxane and acetic acid);

2,3,4,17,18,19,20-heptanor-1,5-inter-m-phenylene-13,14-didehydro-16-methoxy-ethoxy-PGI$_2$-tris-hydroxymethyl-amino-methane salt, $R_f=0.56$ and 0.53 (a 20:20:1 mixture of benzene, dioxane and acetic acid);

2,3,4,17,18,19,20-heptanor-1,5-inter-m-phenylene-13,14-didehydro-16-(2,2,2-trifluoroethoxy)-PGI$_2$-pyrrolidine salt, $R_f=0.59$ and 0.55 (a 20:20:1 mixture of benzene, dioxane and acetic acid);

2,3,4,17,18,19,20-heptanor-1,5-inter-m-phenylene-13,14-didehydro-16-(2-butyn-1-yl-oxy)-PGI$_2$-morpholine salt, $R_f=0.51$ and 0.50 (a 20:10:1 mixture of benzene, dioxane and acetic acid);

2,3,4-trinor-1,5-inter-m-phenylene-5-fluoro-13,14-didehydro-PGI$_2$-triethanolamine salt, $R_f=0.50$ and 0.48 (a 20:10:1 mixture of benzene, dioxane and acetic acid);

2,3,4,17,18,19,20-heptanor-1,5-inter-m-phenylene-5-fluoro-16-(3-trifluoromethyl-phenoxy)-PGI$_2$-calcium salt, $R_f=0.44$ and 0.37 (a 20:10:1 mixture of benzene, dioxane and acetic acid);

2,3,4-trinor-1,5-inter-m-phenylene-13,14-17,18-bis-didehydro-20-methyl-6a-carbaprostaglandine-I$_2$-sodium salt, $R_f=0.61$ and 0.58 (a 20:20:1 mixture of benzene, dioxane and acetic acid);

N-(2,3,4,17,18,19,20-heptanor-1,5-inter-m-phenylene-13,14-didehydro-16-crotyloxy-PGI$_2$-yl)-glycine sodium salt, $R_f=0.39$ (a 20:10:1 mixture of benzene, dioxane and acetic acid).

EXAMPLE 26

Preparation of
2,3,4,17,18,19,20-heptanor-1,5-inter-m-phenylene-13,14-didehydro-16-methoxyethoxy-PGI$_2$-carbethoxy-methyl-amide One proceeds as described in Example 15 except that the mixed anhydride of 2,3,4,17,18,19,20-heptanor-1,5- inter-m-phenylene-13,14-didehydro-16-methoxyethoxy-PGI$_2$ formed with chloro isobutyl formiate is reacted with 714.5 mg (6.93 millimoles) of glycine ethyl ester. Thus 2.862 g of the title compound are obtained, yield 91.3%.

Analytical data: TLC: R$_f$=0.49 (a 20:20:1 mixture of benzene, dioxane and acetic acid). $^1$H-NMR (CDCl$_3$, δ): 7.1–8.1 (m, 4H, aromatic H), 5.9 (s, H-5 E isomer), 5.25 (s, H-5, Z isomer), 3.75–4.5 (m, 7H, H-9, H-11, H-15, OC$\underline{H}_2$, NHC$\underline{H}_2$), 0.85 (t, 3H, C$\underline{H}_3$).

In an analogous manner to the above process the following compounds are prepared:

2,3,4-trinor-1,5-inter-(4-chloro-1,3-phenylene)-13,14-didehydro-PGI$_2$-amide, R$_f$=0.52 and 0.50 (ethyl acetate);

2,3,4-trinor-1,5-inter-(4-fluoro-1,3-phenylene)-13,14-didehydro-20-ethyl-PGI$_2$-diisopropylamide, R$_f$=0.63 and 0.50 (ethyl acetate);

2,3,4-trinor-1,5-inter-(6-acetamido-1,3-phenylene)-13,14-didehydro-20-ethyl-PGI$_2$-α-methyl-benzylamide, R$_f$=0.37 and 0.34 (ethyl acetate);

2,3,4,17,18,19,20-heptanor-1,5-inter-m-phenylene-16-(3-chloro-phenoxy)-PGI$_2$-pyrrolidide, R$_f$=0.55 (ethyl acetate);

2,3,4,17,18,19,20-heptanor-1,5-inter-m-phenylene-16-crotyloxy-PGI$_2$-anilide, R$_f$=0.58 and 0.52 (a 1:1 mixture of dichloro methane and acetone);

2,3,4,17,18,19,20-heptanor-1,5-inter-m-phenylene-13,14-didehydro-16-methoxyethoxy-PGI$_2$-1-hydroxy-2-butyl-amide, R$_f$=0.18 and 0.11 (ethyl acetate).

EXAMPLE 27

Preparation of 2-decarboxy-2-cyano-2,3,4-trinor-1,5-inter-m-phenylene-13,14-didehydro-16-methoxyethoxy-PGI$_2$ One proceeds according to Example 16 except that 680 mg (169 millimoles) of 2,3,4-trinor-15-inter-m-phenylene-13,14-didehydro-16-methoxyethoxy-PGI$_2$ amide are used. Thus 413.75 g of the title compound are obtained, yield 63.7%.

Analytical data: TLC: R$_f$=0.60 and 0.55 (ethyl acetate). $^1$H-NMR (CDCl$_3$, δ): 7.2–8.25 (m, 4H, aromatic H), 5.9–5.27 (s, and s, H-5, E and Z isomers), 3,45–4,3 (m, 9H, C$\underline{H}$O).

EXAMPLE 28

Preparation of 2-decarboxy-2-(1H-tetrazole-5-yl)-2,3,4,17,18,19,20-heptanor-1,5-inter-m-phenylene-16-crotyloxy-PGI$_2$ One proceeds according to Example 17 except that 2,3,4,17,18,19,20-heptanor-1,5-inter-m-phenylene-16-crothyloxy-PGI$_2$-amide is used. Thus 2,38 g of the title compound are obtained, yield 60.3%.

Analytical data: R$_f$=0.04 (a 20:10:1 mixture of benzene, dioxane, and acetic acid). $^1$H-NMR (CDCl$_3$, δ): 7.35–8.4 (m, 4H, aromatic H), 5.2–5.95) m, 5H, olephinic H), 1.48) d, 3H, =CH—C$\underline{H}_3$).

EXAMPLE 29

Preparation of 2,3,4-trinor-1,5-inter-m-phenylene-13,14-didehydro-20-ethyl-PGI$_2$-methanesulfonamide One proceeds according to Example 18 except that 2,3,4-trinor-1,5-inter-m-phenylene-13,14-didehydro-20-ethyl-PGI$_2$-methyl ester is used. Thus 2.05 g of the title compound are obtained, yield 71%.

Analytical data: R$_f$=0.1 (a 20:10:1 mixture of benzene, dioxane and acetic acid). $^1$H-NMR (CDCl$_3$, δ): 7.25–8.3 (m, 4H, aromatic H), 5.2–5.9 (s, H-5, E és Z isomers), 3.0 (s, 3H, C$\underline{H}_3$), 0.87 (t,3H, C$\underline{H}_3$).

What is claimed is:

1. A compound of the Formula (I)

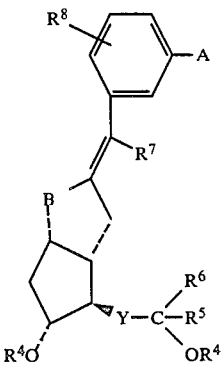

wherein

A stands for carboxy, cyano, tetrazolyl or —COOR$^3$ or —CONR$^1$R$^2$;

R$^3$ is C$_{1-4}$ alkyl or an equivalent of a pharmacologically acceptable cation;

R$^1$ and R$^2$ each stands for hydrogen, phenyl; C$_{1-5}$ alkyl optionally substituted by carboxy, hydroxy, phenyl or C$_{2-5}$ alkoxycarbonyl; or C$_{1-4}$ alkylsulfonyl; or R$^1$ and R$^2$ together form an α, ω-alkylene chain containing 3–6 carbon atoms;

B stands for oxygen;

Y is optionally bromo-substituted vinylene or a —C≡C— group;

R$^4$ stands for hydrogen or tetrahydro-pyran-2-yl;

R$^5$ represents an alkyl group containing 5–9 carbon atoms, which can be optionally interrupted by one or more oxygen atoms or —CH=CH— or C≡C groups and/or optionally substituted by halogen; or a phenoxymethyl group optionally substituted by halogen or trifluoromethyl; or an alkenoyloxymethyl group containing 3–5 carbon atoms in the alkenoyl group;

R$^6$ is hydrogen or C$_{1-4}$ alkyl;

R$^7$ stands for hydrogen, halogen, cyano, C$_{1-4}$ alkyl or C$_{1-4}$ alkoxy;

R$^8$ is hydrogen, halogen, cyano, nitro, hydroxy or C$_{2-5}$ alkanoylamido;

with the proviso that if

R$^5$ stands for an alkyl group containing 5 to 9 carbon atoms or haloalkyl with 5 to 9 carbon atoms, or a phenoxymethyl group optionally substituted by halogen or trifluoromethyl, then either R$^7$ is other than hydrogen, or C$_1$ to C$_4$ alkyl, or R$^8$ is other than hydrogen, or A is other than carboxy or —COOR$^3$, or a salt thereof formed with a pharmaceutically acceptable cation.

2. The compound of the formula (I) defined in claim 1 selected from the group consisting of:

2,3,4-trinor-1,5-inter-m-phenylene-13,14-didehydro-20-methyl-Δ$^{19}$-PGI$_2$;

2,3,4-trinor-1,5-inter-m-phenylene-13,14-17,18-bis-didehydro-20-methyl-PGI$_2$ sodium salt; and 2,3,4-trinor-1,5-inter-(4-fluoro-1,3-phenylene)-13,14-didehydro-20-methyl-PGI$_2$ sodium salt.

3. The salt of the formula (I) defined in claim 1 wherein A is —COONa, $R^8$ is hydrogen, $R^6$ is hydrogen, Y is —C≡C—, $R^5$ is n-hexyl, and $R^7$ is F, Cl, $CH_3O$— or —CH.

4. The salt of the formula (I) defined in claim 1 wherein A is —COONa, $R^4$, $R^6$, $R^7$ and $R^8$ are each hydrogen, Y is —C≡C— and $R^5$ is 2-methyl-4-pentyn-1-yl; 6-methyl-5-hepten-1-yl; —$CH_2O$—$CH_2$—$CH_2$—$OCH_3$; or —$CH_2O$—$CH_2$—$CF_3$.

5. A pharmaceutical composition having prolonged cytoprotective, thrombocyte aggregation inhibiting and a low hypotensive effect comprising a pharmaceutically effective amount of a compound of the formula I according to claim 1, or a salt thereof formed with a pharmacologically acceptable cation in admixture with a suitable, inert, usual pharmaceutical carrier, filler, diluent or auxiliary agents.

6. A method of treating an animal subject in need of a prolonged cytoprotective, thrombocyte aggregation inhibiting, and a low hypotensive effect which comprises the step of administering to said animal subject a pharmaceutically effective amount of the compound of the formula (I) defined in claim 1 or a salt formed thereof with a pharmacologically acceptable cation.

* * * * *